US011931183B2

(12) United States Patent
Dillman Taylor et al.

(10) Patent No.: US 11,931,183 B2
(45) Date of Patent: Mar. 19, 2024

(54) COMPUTER ANALYSIS AND ENHANCED VISUALIZATION OF PLAY INTERACTIONS

(71) Applicant: University of Central Florida Research Foundation, Inc., Orlando, FL (US)

(72) Inventors: Dalena Dillman Taylor, Orlando, FL (US); Dave Edyburn, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 995 days.

(21) Appl. No.: 16/862,083

(22) Filed: Apr. 29, 2020

(65) Prior Publication Data

US 2020/0345308 A1 Nov. 5, 2020

Related U.S. Application Data

(60) Provisional application No. 62/841,872, filed on May 2, 2019.

(51) Int. Cl.
*A61B 5/00* (2006.01)
*A61B 5/16* (2006.01)
(Continued)

(52) U.S. Cl.
CPC .......... *A61B 5/6896* (2013.01); *A61B 5/0002* (2013.01); *A61B 5/0077* (2013.01); *A61B 5/16* (2013.01); *A61B 5/165* (2013.01); *A61B 5/168* (2013.01); *A61B 5/744* (2013.01); *A61M 21/00* (2013.01); *A63H 3/003* (2013.01);
(Continued)

(58) Field of Classification Search
CPC ....... A61B 5/6896; A61B 5/165; A61B 5/168; A61B 5/744; A61B 2503/06; A61B 2562/0219; A61B 2562/0247; A63H 3/003; A63H 3/36; A63H 3/02; A63H 33/042; A63H 2200/00; A61M 2205/59
See application file for complete search history.

(56) References Cited

U.S. PATENT DOCUMENTS

2011/0021109 A1* 1/2011 Le ........................... A63H 13/00
446/300
2014/0314327 A1* 10/2014 Elliott ...................... A63H 3/02
382/209
2014/0364240 A1* 12/2014 Leyland .................. A63F 13/77
463/43

FOREIGN PATENT DOCUMENTS

JP 2002536030 A * 10/2002 .............. A63H 3/28
JP 3566646 B2 * 9/2004

* cited by examiner

*Primary Examiner* — Daniel L Cerioni
*Assistant Examiner* — Jonathan E. Cooper
(74) *Attorney, Agent, or Firm* — Anton J. Hopen; Smith & Hopen, P. A.

(57) ABSTRACT

A system of sensors integrated into toys for monitoring free play activity of a human subject wherein patterns in play activity automatically are weighted into a pattern for identification of behavioral milestones, developmental progress and/or behavioral disorders. Specifically, accelerometers detect movement of toys which determine: (1) if the toy is being played with; and (2) the intensity in which the toy is moved. Pressure sensors detect the level and location in which a child may hold a toy. Synchronized with an audio-visual record of the play therapy session and a computer-generated avatar representation of the physical object, this data is integrated to find peak levels of behavior giving clinicians more efficient analytical tools.

9 Claims, 14 Drawing Sheets

(51) Int. Cl.
*A61M 21/00* (2006.01)
*A63H 3/00* (2006.01)
*A63H 3/36* (2006.01)
*G01L 1/20* (2006.01)
*A63H 3/02* (2006.01)
*A63H 33/04* (2006.01)

(52) U.S. Cl.
CPC ................ *A63H 3/36* (2013.01); *G01L 1/205* (2013.01); *A61B 2503/06* (2013.01); *A61B 2562/0219* (2013.01); *A61B 2562/0247* (2013.01); *A61M 2205/59* (2013.01); *A63H 3/02* (2013.01); *A63H 33/042* (2013.01)

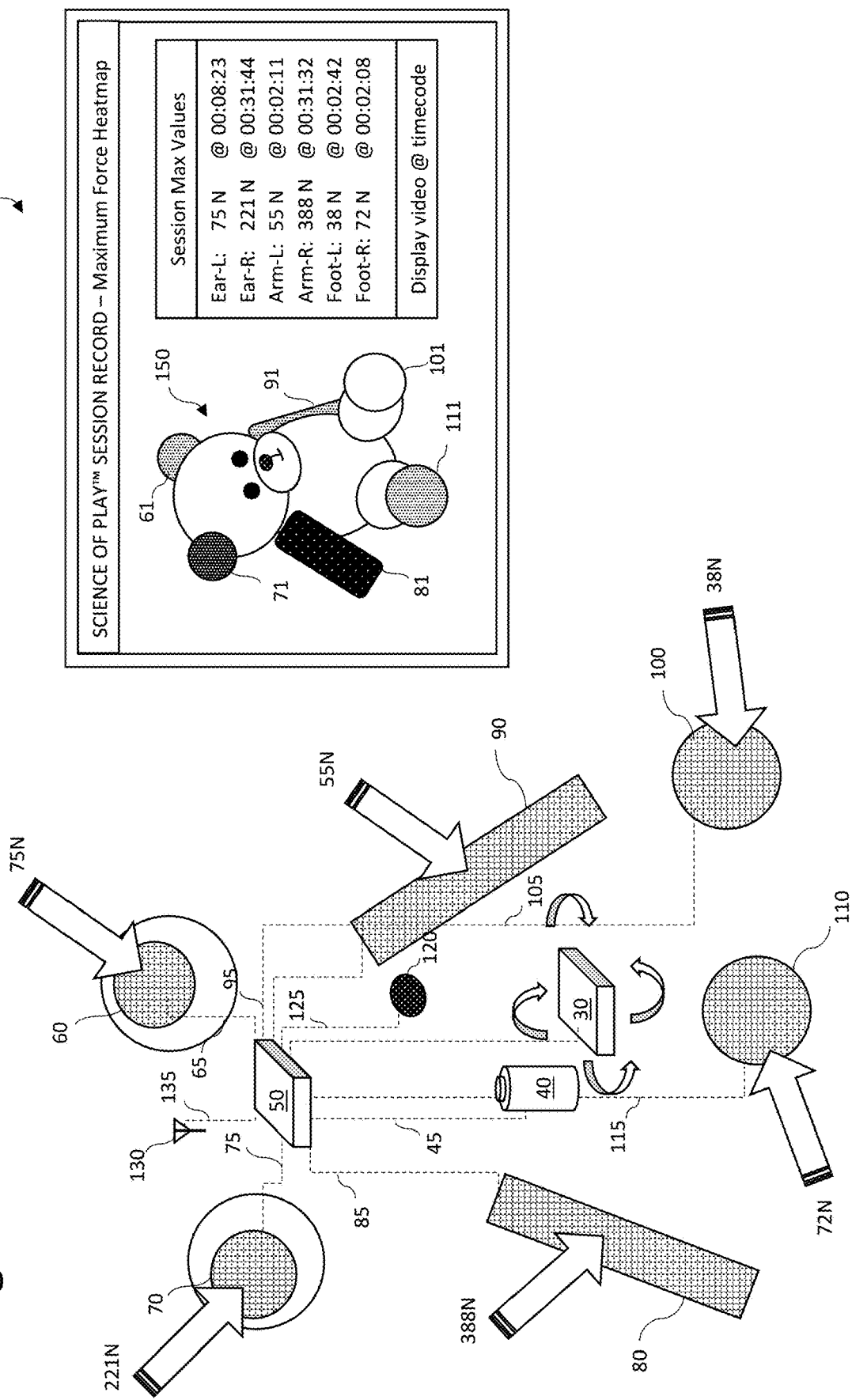

COMPUTER ANALYSIS AND ENHANCED VISUALIZATION OF PLAY INTERACTIONS

CROSS REFERENCE TO RELATED APPLICATIONS

The present application claims the benefit of the filing date of U.S. provisional patent application Ser. No. 62/841,872 filed on May 2, 2019, the disclosure of which is incorporated herein by reference.

BACKGROUND OF THE INVENTION

1. Field of the Invention

This invention relates to behavioral sciences. More specifically, it relates to a system to quantify and analyze interactions with toys for diagnosis of developmental and behavioral condition of a subject.

2. Brief Description of the Related Art

Play is a vital part of children's social, emotional, cognitive, and brain development and is an important vehicle for promoting language, cognition, social competence, and self-regulation. Yet, with increased pressure to perform in school, increased frequency of testing, and the lack understanding of the value of free play on children's overall development, administrators and policy makers have consistently taken action to eliminate play in elementary schools. As a result, there is an urgent need for research to understand how play offers a window into children's developmental trajectories and is predictive of subsequent academic success or failure.

The lack of high-quality play, skills and knowledge necessary for success in school compounds the academic, behavioral, and social-emotional challenges in school for the most vulnerable students. With the decline of play in elementary schools, both as a pedagogical approach to learning in the classroom and with outdoor gross-motor play, teachers have been witness to an increasing number of disciplinary referrals and expulsions, even at the prekindergarten levels, and reports of children unable to meet behavioral and learning expectations in the general education classroom. Also concerning is the overrepresentation of children from low-income, second language, immigrant, or racial and ethnic minority households in both exclusionary disciplinary practices and the exceptional education system which is frequently directly correlated with the aforementioned lack of essential social-emotional, self-regulatory, and language skills considered acceptable in schooling.

The United States Center for Disease Control (CDC) reported in 2018 that nearly 2 million (11% of the population surveyed) additional children were diagnosed with Attention Deficit Hyperactivity Disorder (ADHD) from 2003 to 2016, with 62% taking medications for ADHD. Nearly two-thirds of these children with an ADHD diagnosis also have another mental, emotional, or behavioral disorder. However, studies have noted a common belief that only 4% of children are born with ADHD, while other children develop this condition based on environmental influences, reflecting a 'cultural illness' (i.e., lack of play time). As noted previously, play can be a strong protective factor for those children without predispositions to develop mental health problems. By understanding the importance of play, educational professionals can implement play across a continuum to intervene with children at the level of their needs, recognizing that not all children need therapeutic or psychological interventions, but all children need play to grow, develop, and mitigate stressors.

However, when free play no longer addresses the child's emotional and behavioral needs, play therapy has been found to be effective according to pre/post assessment data. According to the Association for Play Therapy (2018), play therapy is "the systematic use of a theoretical model to establish an interpersonal process wherein trained play therapists use the therapeutic powers of play to help clients prevent or resolve psychosocial difficulties and achieve optimal growth and development." Children utilize their natural language of play within a supportive, therapeutic relationship to overcome presenting issues through the development of self-esteem, self-control, and increased coping skills. Researchers have demonstrated the effectiveness of play therapy regardless of age, gender, or presenting issue. Yet, the current issue is that professionals do not understand the how play and play therapy work, rather they only understand that outcomes are more positive for children engaged in play behaviors across settings.

State of Practice:

Play is understood to be a developmentally essential activity for children to build knowledge. Research has found that "play is not a luxury, but rather a crucial dynamic of healthy physical, intellectual, and social-emotional development at all age levels." Further, an American Academy of Pediatrics (AAP) report recommended prescriptions of play, indicating that "play is not frivolous: it enhances brain structure and function and promotes executive function (i.e., the process of learning, rather than the content), which allow us to pursue goals and ignore distractions." However, common practice in schools is to reduce or even eliminate outdoor, gross motor play during recess periods to increase focus on tested subject areas. Therefore, it is becoming increasingly more important for pediatricians to take an active role in promoting the power of play at home during annual well visits.

Teachers, pediatricians, and clinicians value the role play has in the overall learning and well-being of young children. Therefore, play as a learning tool is used frequently in educational and therapeutic settings despite the push back for more didactic instruction and focus on academic testing. However, the extant knowledge base is informed by adult inferences gathered through non-systematic observation. As a result, research on play and play therapy, a developmentally responsive clinical intervention for counseling young children, is less rigorous than would otherwise be possible when informed by quantifiable evidence concerning frequency, duration, and quality of play interactions and analysis of play patterns. This same perspective can be noted across the lifespan, as play is important for overall mental and physical health beyond childhood.

Furthermore, medical fields are moving towards a model of integrative care, which combines primary care and mental health care in one setting. In the current state of practice, children are typical seen by their primary care physician, one of whom does not typically have the mental health training necessary for accurate diagnoses. Given that about approximately 10 million children diagnosed with a mental health issue do not receive adequate treatment on a yearly basis, there appears to be a need for integration of care through a portal network that provides synthesized data regarding the child's developmental, mental, physiological, and psychological stress information via a condensed, individualized treatment plan and report.

However, in view of the art considered as a whole at the time the present invention was made, it was not obvious to those of ordinary skill in the field of this invention how the shortcomings of the prior art could be overcome.

BRIEF SUMMARY OF THE INVENTION

The present invention provides play therapy analytics in a more efficient and insightful view for clinicians. This enables clinicians and therapists to readily identify behaviors of concern from a transformation of sensor data into a new and useful representation of the child's engagement and interaction with toys, environment, and others (i.e., clinician, peers, parents, teachers).

A microcontroller such as those sold under the brands ARDUINO, RASPBERRY PI, ESP32, BEAGLEBOARD, NVIDIA JETSON NANO, ODROID, ADAFRUIT, and TESSEL is affixed inside a physical toy. These devices are classified as a single-board microcontrollers that provide the circuitry needed for many tasks. The components typically include a microprocessor, I/O circuits, a clock generator, RAM, stored program memory and any necessary support integrated circuits (ICs).

A program for ARDUINO hardware may be written in any programming language with compilers that produce binary machine code for the target processor. ARDUINO microcontrollers are pre-programmed with a boot loader that simplifies uploading of programs to the on-chip flash memory. The default bootloader of the ARDUINO UNO is the OPTIBOOT bootloader. A battery inside the physical toy powers the microcontroller, active sensors and transceivers that send the sensor data to remote receivers.

At least one or more pressure sensors are affixed inside or upon the surface of the physical toy. Ideally, there should be no visual or tactile distraction to the child. The physical toys should not immediately convey they are gathering data or else the child may consciously or subconsciously alter otherwise natural behavior.

The pressure sensors are coupled to the microcontroller through an input/output (I/O) connection. The pressure sensors detect force imparted upon them by measuring resistance to an electrical current running through each pressure sensor. In an embodiment of the invention, each sensor is connected to the microcontroller through a dedicated I/O connection wherein the microcontroller instructions poll the plurality of pressure sensors for a value representative of electrical resistance. This value can be translated into a physical force unit such as Newtons. The microcontroller has an internal system clock which can be used to poll the pressure sensors at a predetermine interval. For the purposes of play therapy monitoring, a polling interval of 10 ms, 100 ms, 500 ms, 1 second, or even 2 seconds may still provide sufficient resolution for analysis.

An accelerometer is affixed inside or upon the surface of the physical toy. The accelerometer is connected to the microcontroller through another dedicated I/O connection. Gravitational forces imparted on the physical toy are sensed and communicated to the microcontroller. The accelerometer is useful for several reasons. In a typical play therapy session, a playroom is set up with multiple toys to choose from. The child is permitted to engage in "free play" and thus can select the toy of most interest. The very selection of one toy over another and/or the pattern of play behaviors may have diagnostic implications before the child even starts to play.

When a physical toy is played with, most often it will move and such movement is detectable by the accelerometer. Therefore, simply the binary result of movement or no movement conveys to the microcontroller whether the toy is idle or being played with. Not only does this assist in the generation of a therapy record, it also as a technical value in enabling accelerometers, microcontrollers and transceivers to remain in a low-power state while idle. For example, the microcontroller may be initialized in a low power state and only poll the accelerometer every 5 seconds. However, once the child starts playing with the toy, the microcontroller starts polling the accelerometer every 100 ms or more to capture a greater amount of data on the movement and forces applied to the toy now that it is actively played with.

A transceiver is affixed inside or upon the surface of the physical toy. The transceiver is communicatively coupled to the microcontroller and configured to transmit data collected by the pressure sensors and accelerometer to an external transceiver.

A computer workstation is provided having a processor and computer-readable memory storing software for executing functions and procedures on the processor. For the purposes of this disclosure, "workstation" is considering a computing device that receives sensor and video data for integration. The workstation could be on premise or remotely hosted in a shared facility (e.g., "cloud computing"). The workstation could run server, client or mobile device operating systems.

Communicatively coupled to the workstation is at least one digital camera (such a webcam) to capture video of a play therapy session. The session includes at least one child interacting with the physical toy. It may also include a therapist or clinician observing, directing and/or conversing with the child during the session. The digital camera encodes an audiovisual stream into a storage device (such as a hard drive or cloud storage) as stored video which is accessible by the processor for playback and review.

The computer workstation (e.g., the processor) is connected to the external transceiver which receives timecoded accelerometer and pressure sensor data from the microcontroller in the physical toy during the play therapy session. In an alternative embodiment, the microcontroller itself may use the first transceiver to connect to a WIFI network shared with the computer workstation. In such case, the microcontroller may send data through a representational state transfer (e.g., RESTful web service), typically delivering the data as JSON responses (although flat text files, HTML and XML are other options).

The computer readable instructions in the computer workstation memory generate a graphic avatar representation of the physical toy and modify the visual representation of the avatar responsive to pressure sensor data received from the microcontroller. This graphic avatar representation may be as simple as a 2-dimensional portable network graphic (PNG) file having transparency features all the way up to a 3-dimensional, rigged model of the physical toy object. Ideally, if the physical object is a toy teddy bear, the avatar generated (or rendered) by the computer workstation has a similar appearance. In an embodiment of the invention, the physical toy is imaged on a key-color background and used as the avatar wherein the background is made transparent when rendered by the computer workstation (similar to any chroma-key technology, e.g., "green screen").

A display device such as a computer monitor is communicatively coupled to the computer workstation. The avatar and stored video of the play therapy session are presented on the display device. In synchronization with the timecode of the stored video, the visual representation of the avatar is modified responsive to pressure sensor data. For example, if five minutes into the play session, the child attempts to choke the teddy bear, the pressure sensors polled by the microcontroller detect greater electrical resistance and convey the value and timecode to the computer workstation. The workstation may modify the facial expression of the avatar of the teddy bear to show fear and surprise. This modification may be achieved by developing algorithms that represent ranges of interest for the teddy bear avatar (e.g., happy, fear, surprise, sadness, anger). The modification may be effected by changing variables in the case of a vector presentation of the teddy bear avatar. For example, Bezier curves and splines may be adjusted for smiles, frowns, raised eyebrows and the like. Eyes may be adjusted with a greater diameter to show surprise or modified into ellipses to show skepticism. Alternatively, an array of bitmapped images, each with a variation of expression may be accessible by the computer workstation so that an image replacement of one interest, emotion and/or expression may be achieved. In addition or alternatively, the neck region of the avatar may be shaded or colorized to show the increased pressure. This is referred to as a localized heatmap which typically renders warmer colors (e.g., red) on the spectrum for higher values and colder colors (e.g., blue) for lower values.

An embodiment of the invention records maximum sensor reading values for each sensor and then links each maximum value to the time in the recorded video wherein the event occurred. This done by storing each pressure sensor reading associated with the time code value when the resistance value was obtained. All the resistance values for each pressure sensor are then parsed or queried to retrieve the maximum resistance value for each sensor with the associate timecode representative of the time during the therapy session when the value occurred. For each pressure sensor, the heatmap shown on the avatar conveys the location on the physical toy where the pressure sensor is located, the minimum value of resistance (inversely proportional to the pressure imparted) detected and the timecode value of when the minimum value occurred during the therapy session.

For each minimum value of resistance, the computer workstation displays selectable controls so the end user of the computer workstation can jump directly to the portion of the stored video when the high-pressure event occurred. The clinician present in the room may not have even been aware that the child imparted such force on the store. Taken in the context of the session, it allows the clinician to determine if any extrinsic action or dialog prompted the child's reaction.

An embodiment of the invention provides a natural language processing to discern age appropriate vocabulary as well as terms of clinical significance, generated transcript of the therapy session which is presented in timed synchronization with the stored video. Speech recognition enables the recognition and translation of spoken language into text by computers forming the transcript of the play session. In an embodiment of the invention, the speech recognition is coupled with language translations (e.g., English to Spanish). An array of keywords of clinical significance may automatically generate "bookmarks" or chapter segments in the stored video record whereby a clinician may "jump" or "advance" in the stored video to keywords that are monitored. As noted above, this facilitates the review of the play session, particularly for meaningful physical reactions by the child to dialog.

An embodiment of the invention shows the avatar of the toy concurrently with the stored video, the avatar of the toy having a locality heatmap of each pressure sensor generated in synchronization with the resistance measured at each timecode value. This may be presented side-by-side or the avatar may be overlaid on a Z-axis on top of the stored video of the therapy session.

An array of pressure sensor resistance range values may be stored in memory accessible by the processor, each range value is associated with a distinct level of visual modification to the portion of the avatar of the toy representative of the corresponding portion of the physical toy where the pressure sensor is affixed. For example, from 0-5N, there is no change in the heatmap. From 5-50N, the heatmap portion turns blue. From 50-150 the heatmap portion turns yellow. From 150-250 the heatmap portion turns orange. From 250N and above, the heatmap portion turns red. Embodiments of the invention may also include the physiological condition and movement of the child (as opposed to, or in addition to the toy). As discussed below, respiration, pulse rate, verbalization and movement of the child may be visually represented and/or augmented in the store video media.

BRIEF DESCRIPTION OF THE DRAWINGS

For a fuller understanding of the invention, reference should be made to the following detailed description, taken in connection with the accompanying drawings, in which:

FIG. 2 is an elevated, conceptual view of integrated data sensors and a graphic user interface displaying gathered data.

DETAILED DESCRIPTION OF THE PREFERRED EMBODIMENT

Figure 1:
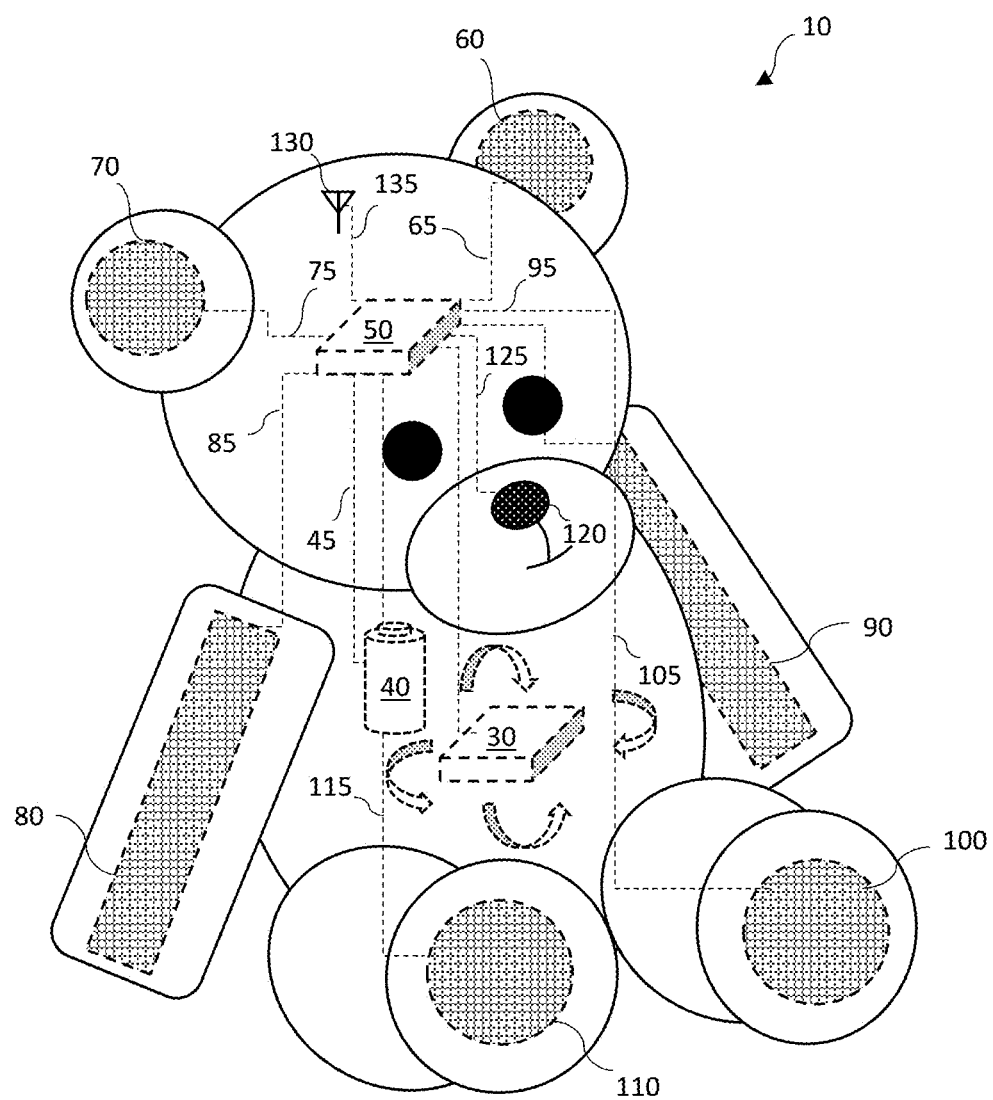
FIG. 1 is an elevated, partially sectional, conceptual view of a toy bear having integrated data sensors.

The present invention is a method and system for gathering behavioral, cognitive, language, observational, and physiological data through cameras, sensors, and devices targeted to reveal a) playful interactions with one's environment, b) relational depth with others (i.e., clinician, peers, parents, teachers), c) coping mechanisms/behavioral responses to combat toxic stress, etc. The play ecology includes toys/objects, movement, interaction transactions, verbal and non-verbal information, and physiological data. In addition, the play ecology includes a system that captures play interactions with one's environment and others; creates a digital transcript of the interactions within a play session; and automates the analysis and reporting of the quality of play interactions to reveal patterns of developmental or clinical interest.

This invention is devoted to the conceptualization, development, and implementation of a system that converts play interactions into a digital format that can be captured, stored, transmitted, manipulated, analyzed, presented, and visualized to improve the efficacy of current practice and to inform data-based decisions concerning the nature and quality of play interactions and patterns. It includes algorithms, data, and proprietary software designed to make meaning from the raw data collected. The invention is novel because there are currently no technologies or systems that enable play researchers to collect and synchronize the multi-modal, multi-channel data generated during play, or to analyze the patterns found within a single play session or across multiple play sessions. The invention has profound implications for the development of evidence-based interventions across disciplines.

One objective of this invention is to develop a comprehensive system that automates the synthetization of data collection to generate a digestible report that can be used across disciplines to inform practice (i.e., healthcare, mental health practice, education, etc.). Given the necessity of integrative care for individuals in today's current practice of medical and non-medical fields, this system enables practitioners across fields to communicate reports of play behaviors and meaning through a portal to aid in possible diagnoses, to generate referrals for follow-up care visits, and to track progress of overall well-being. Further, this system, through the automation of synthesizing data, aids in the development/creation of profiles specific to potential diagnoses, best practices for treatment or intervention for behavioral and emotional concerns, and others across the lifespan. These profiles are transported through a portal to the appropriate recipient (i.e., child's pediatrician, child psychiatrist, school educator).

This invention is applicable to multiple domains, including but not limited to: (1) environments frequented by children, youth, and adults such as home, childcare centers, classrooms, playgrounds and outdoor recreational spaces, and commercial play/recreational spaces/programs; (2) centers that offer individual, group, or family therapy, medical or trauma services, homes, and vehicles; (3) personnel preparation programs, professional development training experiences, workshops, certificate programs, and degree programs related to child development, behavioral and therapeutic interventions for children and/or adults; (4) Alzheimer or dementia services for adults; and (5) animal therapy. Data collected through the Science of Play™ system populates profiles of attitudes, behaviors, developmental milestones, and mental diagnoses as well as develop potential markers that warrant follow-up care or referrals to pediatricians' or psychiatrists' offices. The Science of Play™ system produces data-based reports and visualizations to assess developmental well-being, deficits, and areas of concern as well as suggest interventions that can be used by teachers, mental health providers, physicians, and others. Within the Science of Play™ system, an encrypted portal in which to share this information with the appropriate providers follows current practice of integrative care. This portal follows privacy and security protocols to ensure protection of confidentiality and permission of caregivers/guardians is necessary prior to release of information.

A play therapy session usually includes a number of steps: (1) site preparation; (2) welcoming of parent and child; (3) walk to the playroom; (4) play session itself (typically 45 minutes); (5) return of the child to the parent with brief comments; (6) analysis of the session; and (7) follow up with the parent and child. The duration of the program can last from 1 session to 25 plus sessions, dependent on the presenting concern; therefore, the therapist would need to repeat steps 1-7 equal to the number of play sessions. The present invention involves data collection, analysis, and reporting on metrics in four (4) components of each play therapy session to establish a digital transcript of each session that permits the automation of highlight segments of interest and establish a database that supports manual and automated searching of patterns. Those components are (1) playroom setting; (2) child; (3) therapist; and (4) interaction.

Playroom Setting:

The importance of toy selection is well documented in the literature and yet little is known about the patterns of behaviors with toys across children, sessions, and presenting issues. This invention significantly adds to the science in this area and assists in recognized here-to-for unrecognized patterns.

Ideally, toys are selected for their therapeutic value yet permit children to freely express themselves with few constraints. Different categories of toys may lend themselves for different expression through play. Toy soldiers and weapons may provide means to act out and release aggression. Toys that simulate real-life such as puppets and vehicles may permit direction expression of feelings. Sand, water and paints provide expressive opportunities for the child. Some toys such as dangerous animations may enable children to express feelings of fear.

Referring to FIG. 1, toy bear 10 has embedded force sensing resistors (FSRs) at its left ear 60, right ear 70, right arm 80, left arm 90, left leg 100 and right leg 110. FSRs are passive components that decrease in electrical resistance when there is an increase in the force applied to the active sensor area. FSRs may be embedded internally or on the surface of a toy to measure the pressure imparted on that surface during play therapy. However, when practical, the sensors should not be immediately evident or a distraction from free play with the object.

Figure 9:
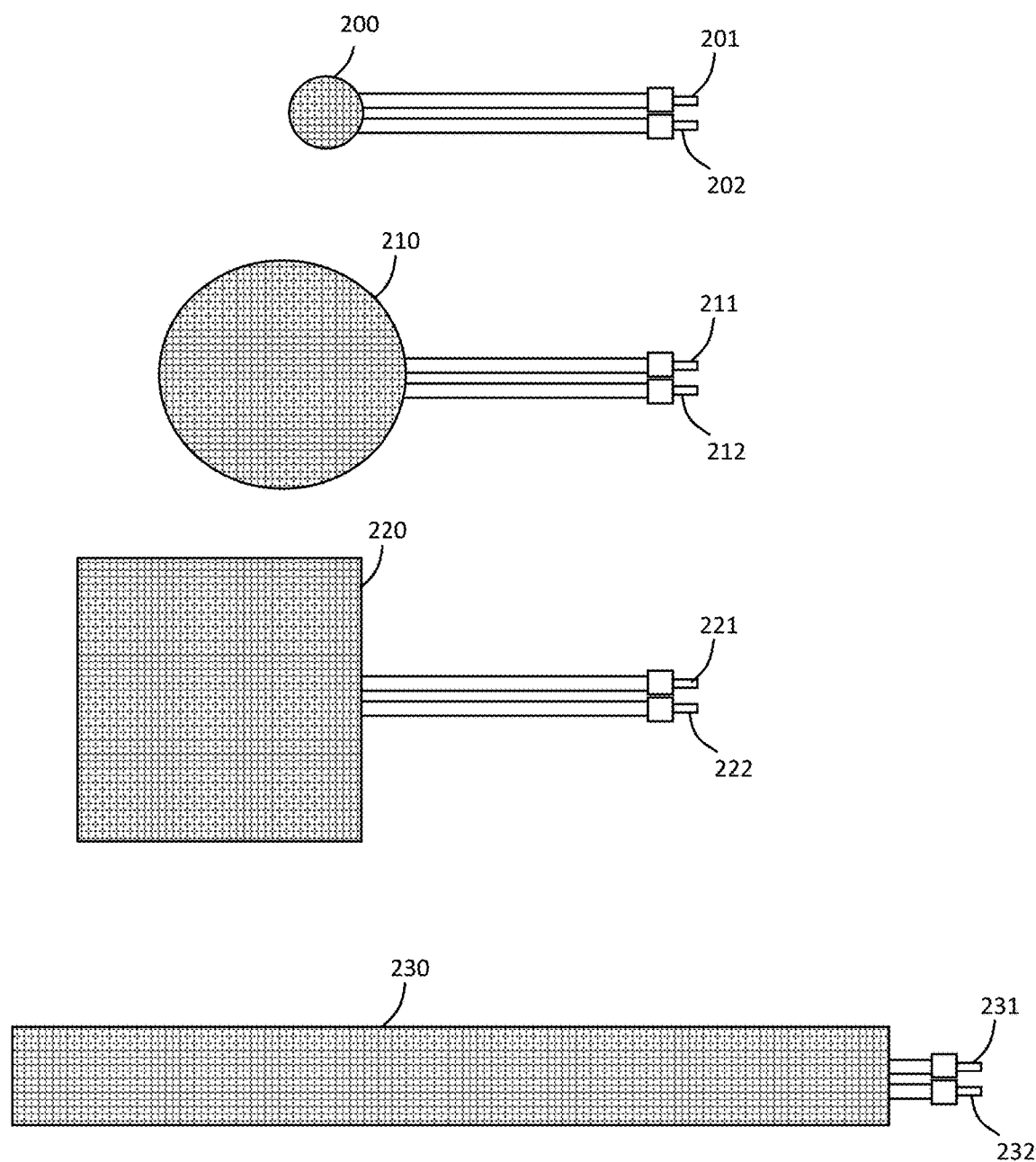
FIG. 9 shows top-down views of polymer thin film (PTF) device pressure sensors in various sizes and shapes for integration into different toys according to the invention.

Variably sized FSRs are available as shown in FIG. 9. Commercially available FSRs (such as those sold under the brand INTERLINK) are flexible, light and approximately 0.02" thin. For example, small circular FSR 200 has two flexible leads (201,202) through which electricity passes and resistance is measured. Larger size FSRs are shown as well: larger circular FSR 210, square FSR 220 and linear FSR 230. The polymer thin film (PTF) device can measure applied forces in ranges from 0.2 to 20 Newtons. However, for detecting greater loads, backings and dispersion mechanics may be deployed.

Figure 10:
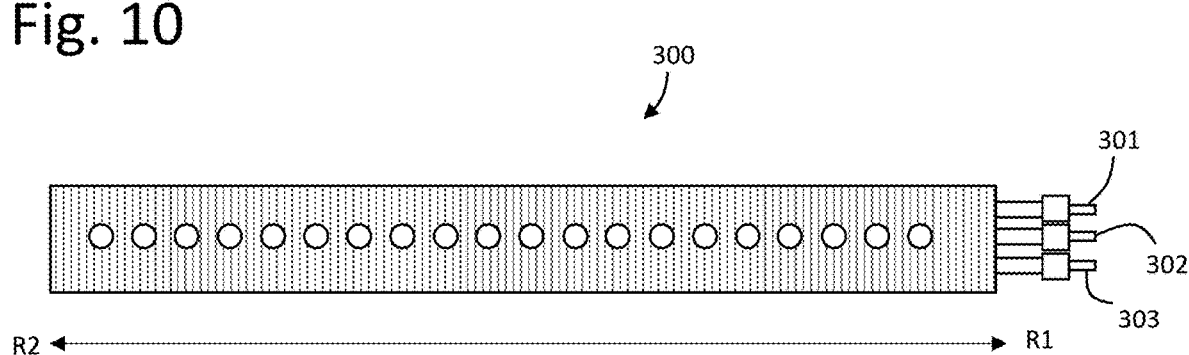
FIG. 10 is a top-down view of a force-sensing linear potentiometer (FSLP).
Figure 11:
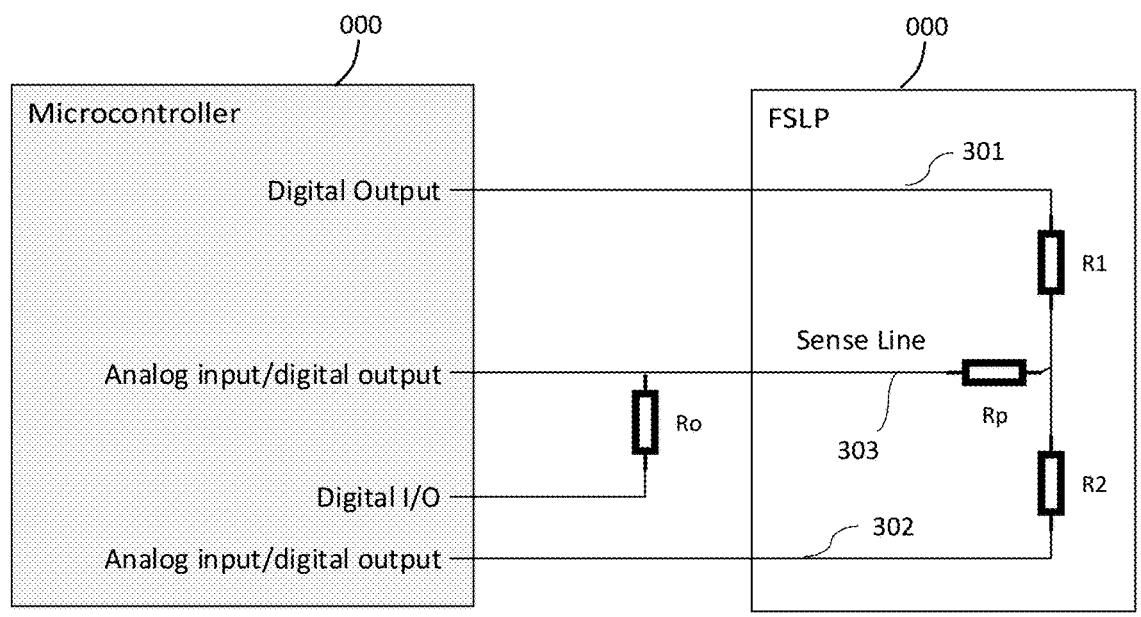
FIG. 11 is a circuit diagram for connecting a FSLP to a microcontroller.

A slightly more advanced FSR is called a force-sensing linear potentiometer (FSLP) as shown in FIG. 10. A FSLP may be integrated to toy bear 10 if more precise location data is desired. The FSLP is a passive component with internal resistances that independently change responsive to the intensity and location of an applied force. This enables a microcontroller with an analog-to-digital converter (ADC) to locate where and how hard the strip is being pressed. For example, an FSLP may be placed at various points within or on an animal toy (anthropomorphic or otherwise) to quantify the timing, frequency, location and intensity (or pressure) of physical interaction between a child and the toy. FSLPs are typically three-terminal devices. When pressure is applied, an internal circuit acts as a three resistors. To obtain the magnitude of the pressure imparted on the toy, an external resistor must be added to the circuit so that four (4) microcontroller lines are needed. An example circuit is shown in FIG. 11. Of the of the lines must be capable of reading analog voltages. Resistance Rp is contingent on the magnitude of the of applied pressure. For example, a FSLP sold under the brand INTERLINK senses pressure wherein resistance changes from approximately 300 kΩ at light touches to around 1 kΩ when pressing firmly.

Turning back to FIG. 1, the FSRs (60, 70, 80, 90, 100 and 110) are coupled to a microcontroller 50 with an analog-to-digital converter (ADC) such as those sold under the ARDUINO or A-STAR brands. For example, the ARDUINO LEONARDO and A-STAR 32U4 PRIME LV models both support twelve (12) analog inputs and over twenty user I/O lines out-of-the-box. As shown in FIG. 1, FSR 60 is coupled to microcontroller 50 through connection 65 (represented as a single line but carries two wires to measure resistance). FSR 70 is coupled to microcontroller 50 through connection 75 and so on. Battery 40 supplies power to microcontroller 50 and any other active sensor embedded into toy bear 10. Accordingly, for most toy interactions, this provides a substantial number of pressure points to monitor as the child interacts with the toy.

In addition to pressure sensing, the present invention also monitors movement of the toy bear 10. This is accomplished through an inertial measurement unit 30 (IMU). IMUs are electronic devices that measure and report orientation, velocity and gravitational forces through the use of accelerometers, gyroscopes and sometimes magnetometers. One example of a highly integrated IMU is an orientation sensor sold under the REDSHIFT LABS brand, model UM7. The UM7 has a 3-axis accelerometer, rate gyro and magnetometer. What is particularly useful is that it has its own microprocessor applying an Extended Kalman Filter to generate attitude and heading estimates. Although more costly than less sophisticated IMUs, the UM7 does preprocessing to reduce the amount of raw data that must be processed downstream. Microcontroller 50 is coupled 135 to transceiver 130 which transmits the FSR and IMU data to a workstation or server. The transmission may be in real-time during the play session or may be cached and downloaded later. An alternative embodiment of the invention may store the data on a computer-readable medium within the toy (such as a secure digital chip) which can be later removed and downloaded for analysis.

In FIG. 2, the internal electronics of toy bear 10 are shown. Arrows show the imparting of force on all of the FSRs. For example, 75N on FSR 60; 221N on FSR 70; 388N on FSR 80; 55N on FSR 90; 38N on FSR 100 and 72N on FSR 110. An aspect of the present invention is that the physical toy object 10 has an avatar counterpart in the associated computer analysis display interface 140. In this case, the physical toy bear 10 of FIG. 1 has a corresponding bear avatar 150 in the display interface 140. In the display interface 140, a maximum force heatmap is displayed on bear avatar 150 wherein darker shades (or warmer colors on a color palette) indicate greater pressure detection over a play therapy session.

For example, the highest force imparted was 388N upon FSR 80 at 31 minutes, 32 seconds into the therapy session. Visually, the intensity of the 388N force upon FSR 80 is shown in bear avatar 150 as heatmap locality 81. The lowest maximum force reading of any sensor was 38N on FSR 100 which occurred at 2 minutes, 42 seconds into the therapy session on toy bear 10's left leg. On bear avatar 150, heatmap locality 101 shows no change in shading or color because the 38N value falls under a threshold set for activating a heatmap indicium. Bear avatar 150 shows the maximum 75N force imparted on FSR 60 at 8 minutes, 23 seconds into the therapy session as heatmap locality 61. Bear avatar 150 shows the maximum 221N force imparted on FSR 70 at 31 minutes, 44 seconds into the therapy session as heatmap locality 71. Bear avatar 150 shows the maximum 55N force imparted on FSR 90 at 2 minutes, 11 seconds into the therapy session as heatmap locality 91. Finally, bear avatar 150 shows the maximum 72N force imparted on FSR 110 at 2 minutes, 8 seconds into the therapy session as heatmap locality 111. Reporting these maximum values both through timecode and visually on the avatar assist in the rapid analysis and therapeutic evaluation of a play session. A link under the session maximum force values notes that clicking on the timecode link causes the software to display the audiovisual record of the play session at the point in time of the maximum force value obtained for the monitored FSR. Alternatively, or in addition, a clickable image map of bear avatar 150 allows the end user to select the heatmap locality of interest and jump to that audiovisual segment as shown in FIG. 3A.

Figure 3A:
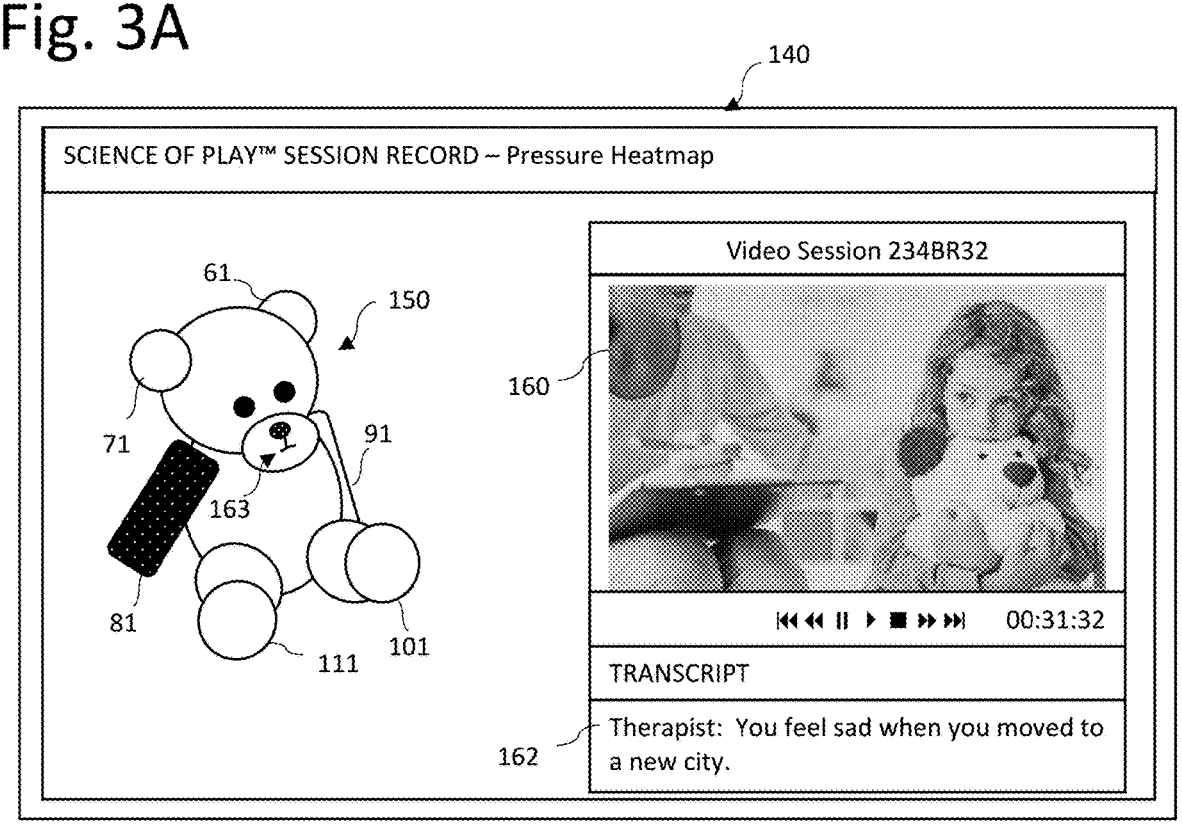
FIG. 3A is a graphic user interface showing maximum force applied on a toy bear upon its right arm and associated timecode video of the physical bear and child during a play session.
Figure 3B:
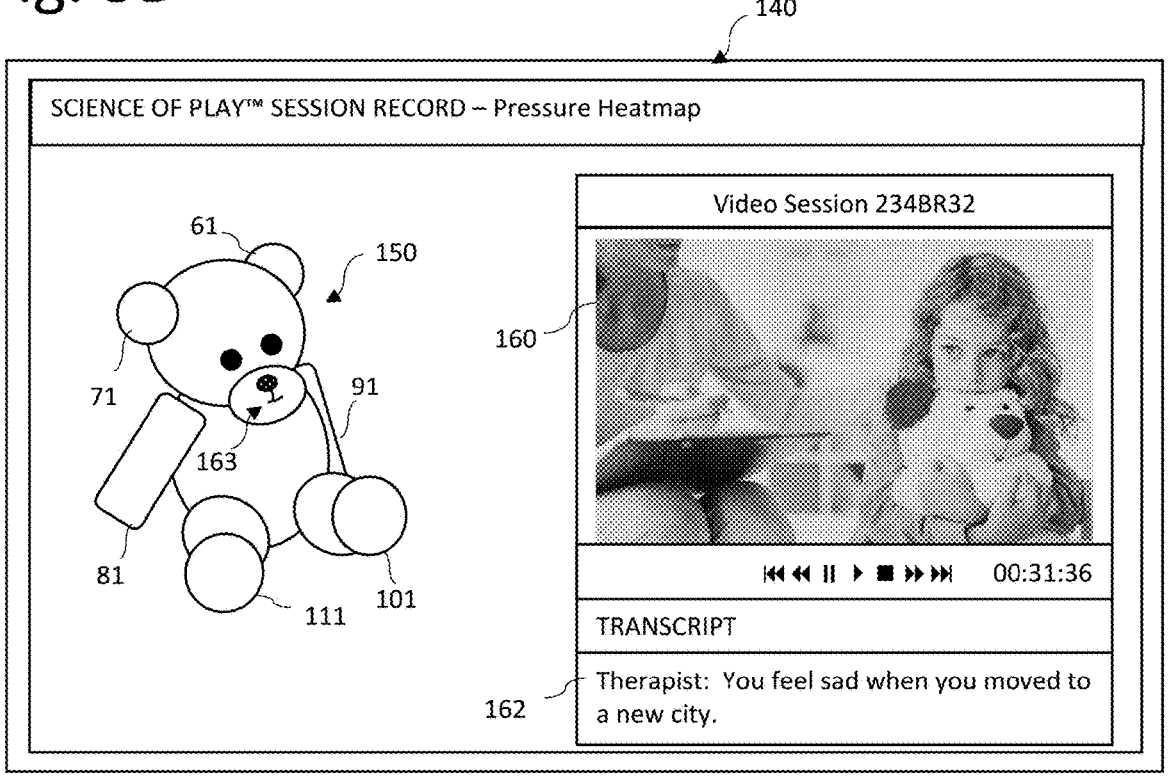
FIG. 3B is a graphic user interface showing little or no force applied on a toy bear upon its right arm and associated timecode video of the physical bear and child during a play session.

Turning now to FIG. 3A, is can be seen that only heatmap locality 81 is shown on bear avatar 150. However, to the right on display interface 140, the audiovisual record of the therapy session is show in a component window at 31 minutes, 32 seconds into the therapy session . . . at the exact time the maximum force value (inversely, minimum electrical resistance) for FSR 80 was detected on toy bear 10's right arm. As shown in video window 160, a child (right) is clutching toy bear 10's right arm while therapist (left) sits slightly behind and to the left of the child. The child's body and arms occlude the view of the therapist and without the sensor data, the therapist would be unaware of the amount of force (if any) the child is imparting onto toy bear 10 and where. Therefore, the therapist and others may not only conduct post-session analytics, they were able to "jump" to the most relevant points in the therapy session for examination. In addition, speech-to-text processing of the audio of the play session form a transcript 162 so that the analysis can quickly associate what dialog may be relevant to the child's behavior and reaction.

Bear avatar 150 can convey more than simply pressure indicia. Bear avatar 150 expression 163 is modified at a predetermined sensor threshold. This threshold could be 100N, 200N or a setting as determined under the circumstances and child's physical abilities. The change in expression can be solely associated with the detected FSR or can be for other sensors or a combination thereof. For example, if the child starts talking in a much higher volume or yells, microphone 120 on toy bear 10 records the audio level which is conveyed to the microcontroller 50. If the audio level exceeds a certain decibel level, timbre or pitch associated with distress, expression 163 on bear avatar 150 changes to express concern, sadness, anxiety or the like. Extrinsic sensors such as those affixed to the body of the child measuring heartrate and breathing can convey indicia on bear avatar 150. For example, if respiration of the child in therapy exceeds a baseline, the torso of bear avatar 150 may be enlarged and reduced visually to simulate heavier respiration. Accordingly, the bear avatar 150 can convey not just what the physical toy bear 10 is experiencing, but also simulate physiological aspects of the child's behavior as well. In FIG. 3A, expression 163 on bear avatar 150 conveys a frown at the timecode value of 31 minutes, 32 seconds. This is because a high level of force was detected at FSR 80. However, only 4 seconds later, the child relaxes her grip on toy bear 10 and FSR 80 shows little to no force imparted. Accordingly, the heatmap locality 81 returns to its base state (e.g., unshaded or white).

This demonstrates an important aspect of the invention. The child's reaction was highly transitory and entirely non-visual to the play therapist but recorded and represented visually both through the heatmap and the bear avatar 150's expression. Furthermore, to facilitate efficient review, the timecode into the session of this reaction was noted with precision and the session review was able to automatically advance to the most relevant portion of the audiovisual record and associated transcript. This allows faster and more effective diagnosis and treatment of the child than currently available.

Figure 4:
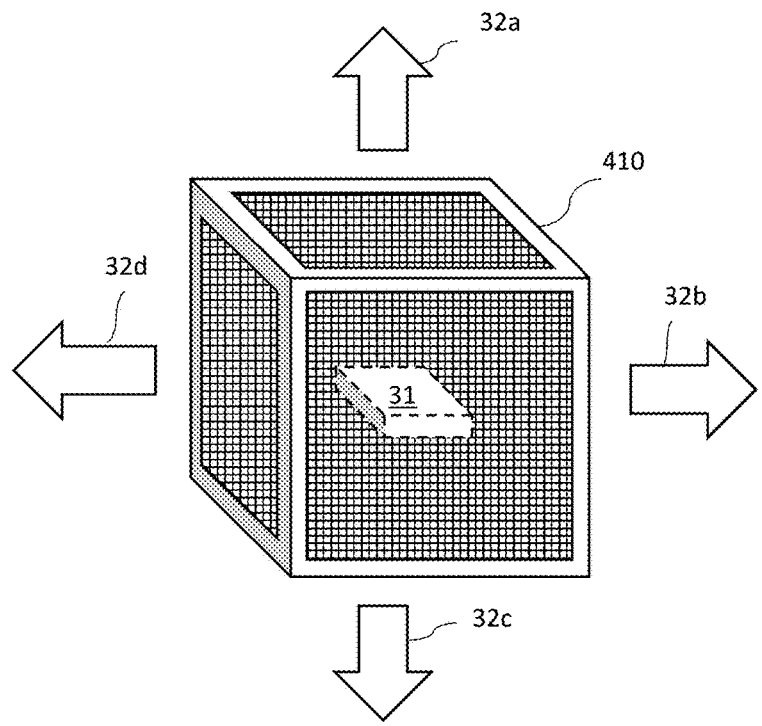
FIG. 4 is a partially sectional, isometric view of a block toy with an integrated IMU.
Figure 5:
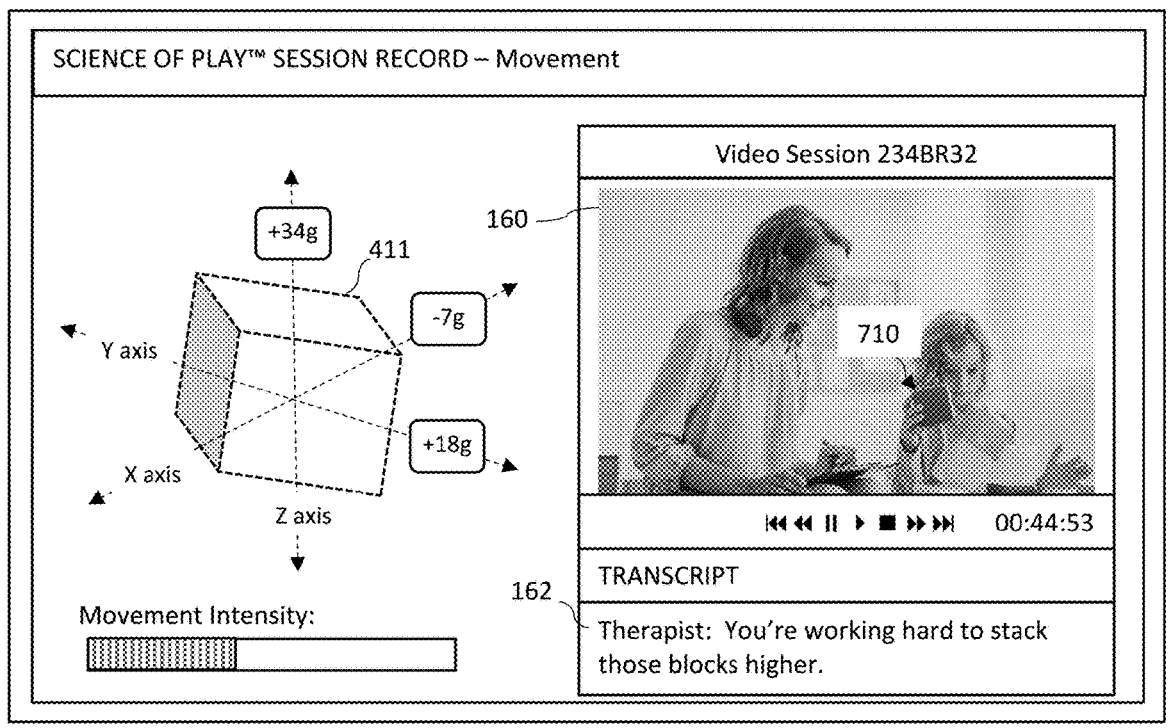
FIG. 5 is a graphic user interface showing an avatar of the play block toy in FIG. 4 with IMU-gathered gravitational data alongside the physical block toy counterpart in recorded video at the same time during the play session.

In FIG. 4, toy block 410 has an internal IMU 31 that detects movement and acceleration. IMU 31 may initialize in a low-power state polling its accelerometer sensor infrequently. However, upon movement, the IMU powers up to convey its movement as shown in display interface 141. Avatar block 411 is a virtual presentation of physical black 710 shown in video play 160. IMU 31 conveys gravitational forces each X, Y and Z axis as conveyed by avatar block 411. FSRs may be integrated upon one or more faces of toy block 410 but in the embodiment conveyed, only the IMU 31 sensor conveys data. Avatar block 411 in FIG. 5 shows a 34 g force imparted upon the Z-axis, a −7 g force upon the X-axis and an 18 g force imparted on the Y-axis. Similar as enumerated above, the maximum gravitational force imparted on toy block may be associated with a specific time instance in the audiovisual record. In other words, vigorous shaking or slamming down of the toy block 410 may be an indicium of aggression or other behavioral reaction needed a more detailed review. The sensor data is timecoded so it can be synchronized with the audiovisual record and/or transcript of the therapy session to more rapidly identify instances of concern.

Figure 6:
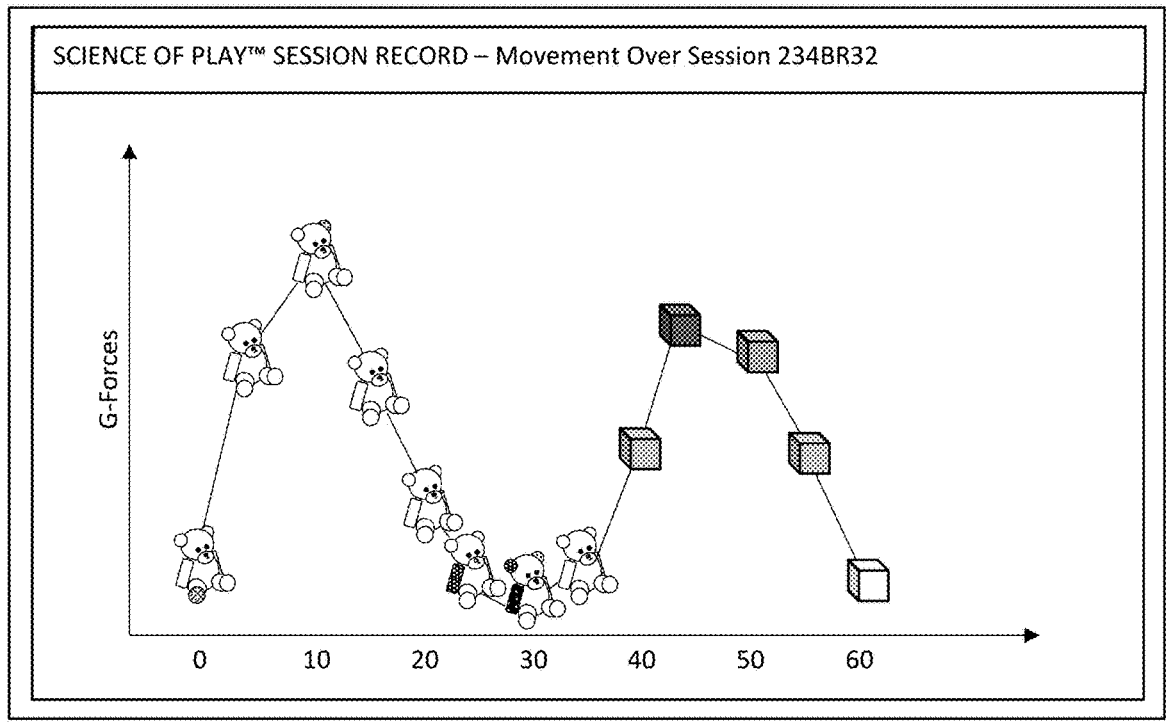
FIG. 6 is a graphic user interface showing a line graph over an hour-long therapy session wherein accelerometer values are shown on the Y-axis and time on the X-axis. Data points convey pressure sensor values detected on the physical toy as heatmaps on avatar representations of the physical toy.

FIG. 6 shows a line graph of object movement in a 60-minute play therapy session. As shown, the child initially played with the toy bear 10 for approximately 40 minutes. Then, the child played with toy block 410. The X-axis is the time into the session and the Y-axis represents the gravitational force imparted on the toy object as obtained through one or more accelerometers. A key innovation in this graph is the use of the toy's avatar as data points in the line chart wherein the heatmap shows FSR values. For example, each heatmap locality is accurately conveyed according to the timecode of the therapy session for bear avatar while FSR-detected force upon toy block 510 changes the shading/color of the avatar block 411. While this line graph is multi-dimensional as to time, force and movement, additional data may be integrated. For example, the size of the datapoint label may be increased or decreased in size based on other timecoded data such as child heartrate, verbalization of the child (talkative, volume, pitch, etc. . . . ), temperature of the child and the like.

Figure 7:
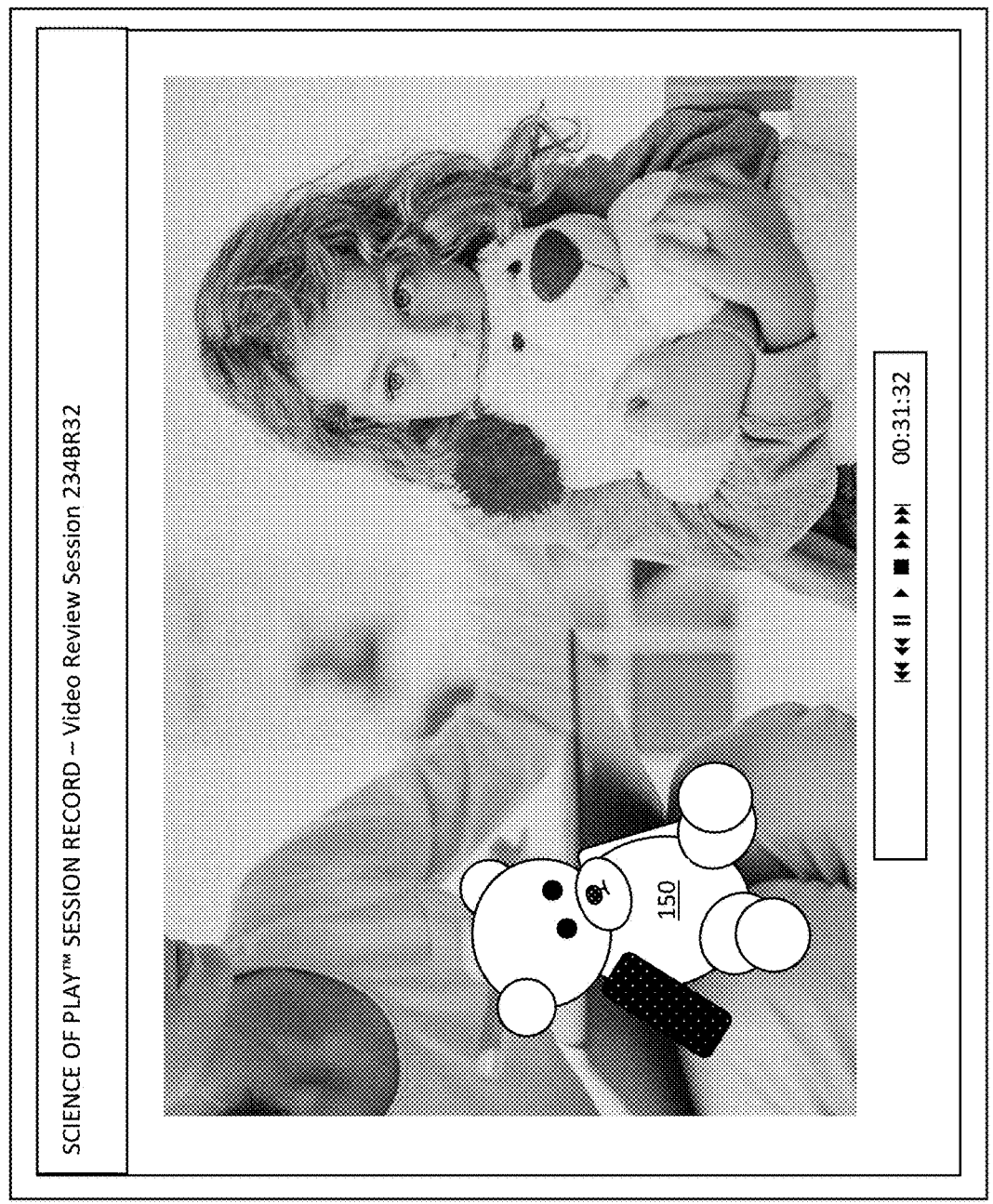
FIG. 7 is a graphic user interface showing an avatar teddy bear overlaid upon a video playback of a therapy session at a time value wherein the maximum sensor force was detected on the physical teddy bear's right arm which is conveyed on the avatar teddy bear as a darkened shape (heatmap).
Figure 8:
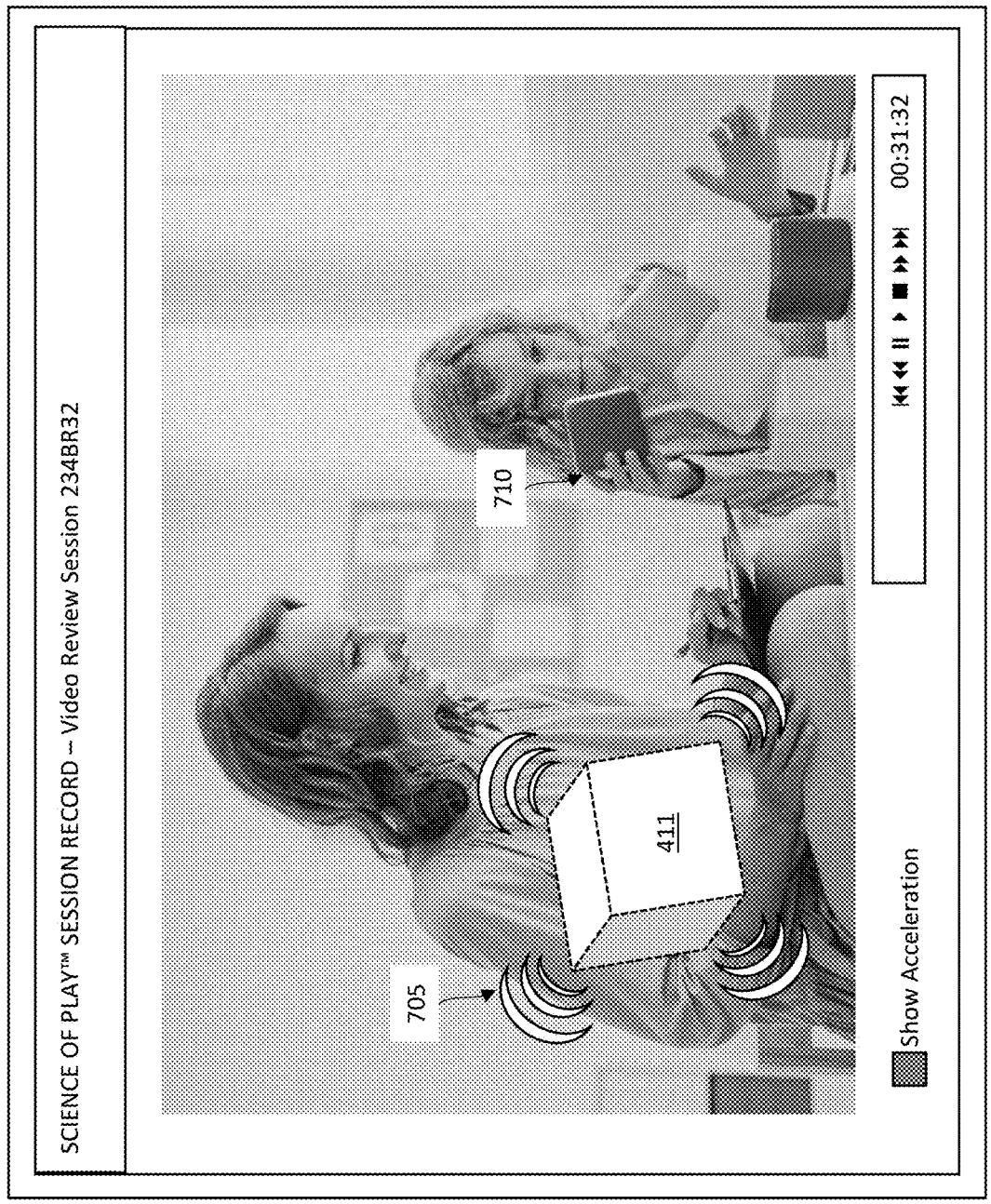
FIG. 8 is a graphic user interface showing an avatar block overlaid upon a video playback of a therapy session. Indicia around the avatar convey gravitational values obtained by accelerometer data from embedded sensors in the physical block manipulated by the child in the session.

FIG. 7 shows yet another embodiment of the invention wherein the toy bear avatar 150 overlays the audiovisual record of the play session. This particular example shows the maximum force imparted on any FSR in the session at 31 minutes, 32 seconds. FIG. 8 similarly shows an avatar block 411 overlaid onto the audiovisual record associated with toy block 710. To convey movement of the toy block 710, visual indicators 705 may be generated around the avatar block 411 to more visually show movement. This may also be represented by rapidly oscillating the avatar block 411 several pixels back and forth to convey the movement not readily apparent from the audiovisual record.

Figure 12:
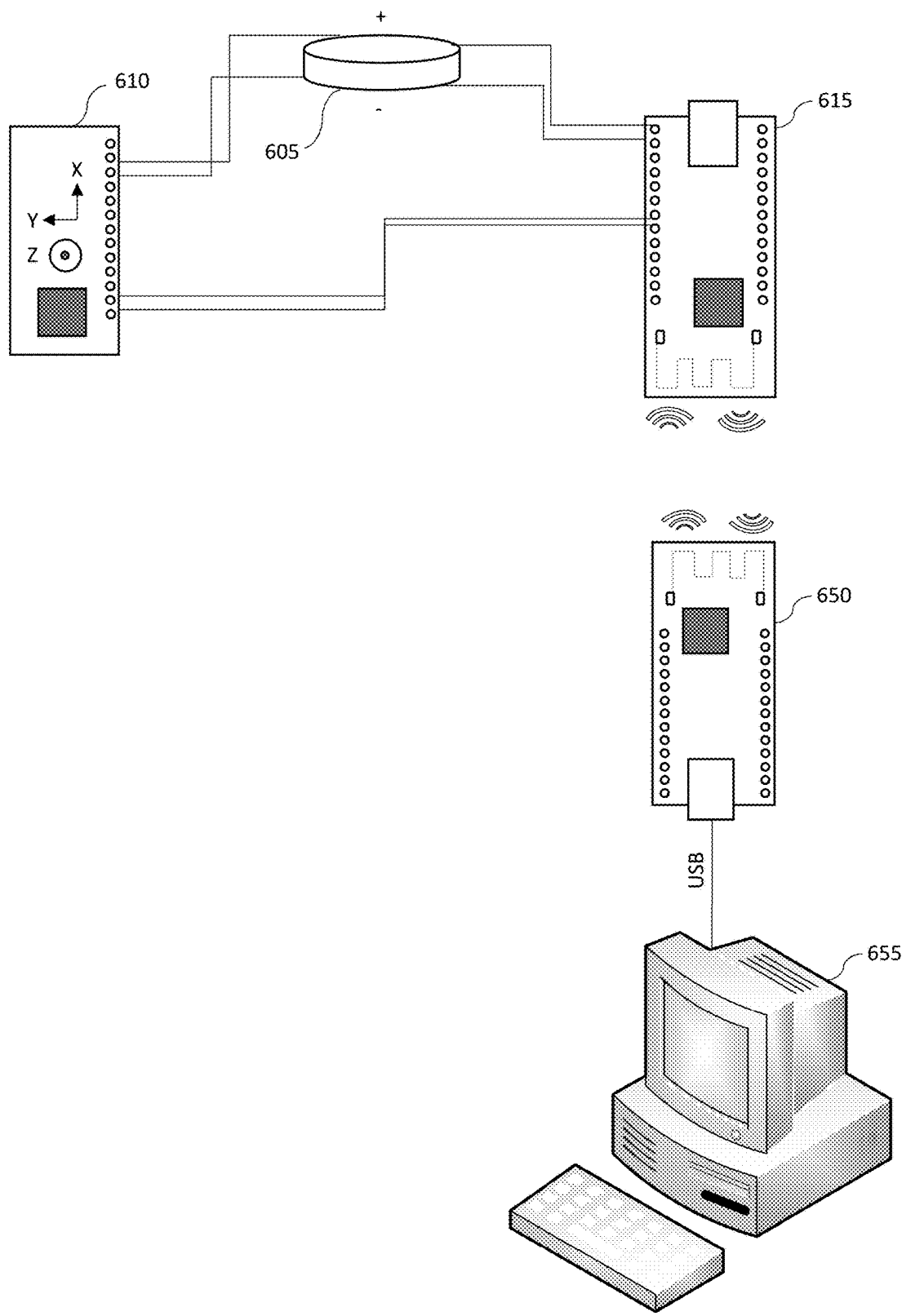
FIG. 12 is a diagrammatic view of an accelerometer coupled to a transceiver to send movement information to another transceiver coupled to a workstation computer.

In FIG. 12, accelerometer 610 is powered by battery 605 and coupled to first transceiver 615. An example of just such a transceiver is sold under the brand POLOLU WIXEL which operates on the 2.4 GHz spectrum. This transceiver is appropriate for smaller toys and can also act as a microcontroller when coupled with sensors like accelerometer 610. First transceiver 615 is powered by a dime-sized 3V battery 605. The WIXEL-brand component is 0.7×1.5" and 3.2 g with an indoor range of about 50 feet. At a desktop computer 655, second transceiver 650 receives timecode and accelerometer data from first transceiver 615. Second transceiver 650 uses a USB connection with desktop computer 655 for both power and data. A single transceiver can use 256 channels so many toys can be simultaneously monitored.

Figure 13:
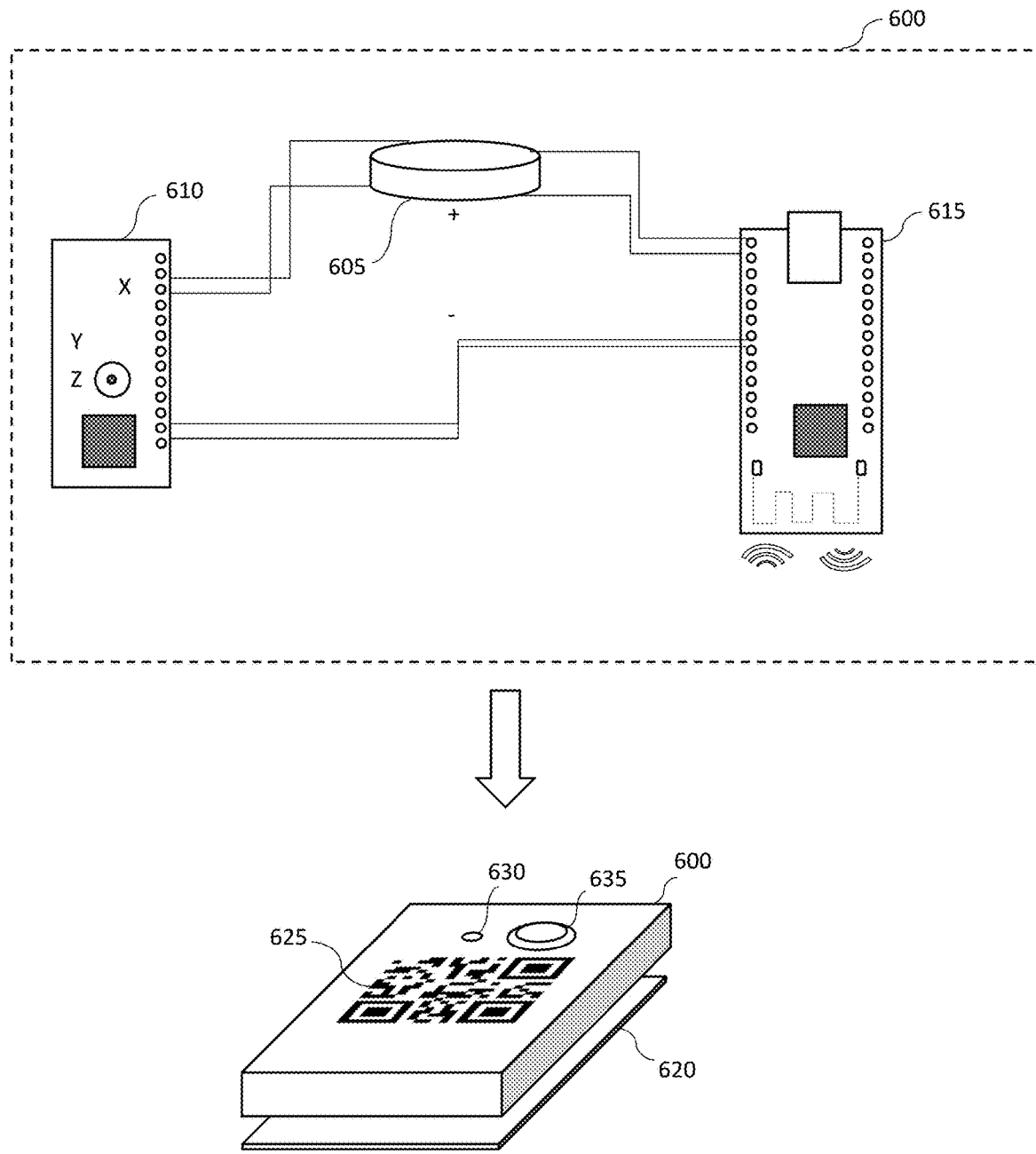
FIG. 13 shows diagrammatic and isometric views of an accelerometer-transceiver component housed into a small, adhesive unit to be affixed to toys to monitor their movement.
Figure 14:
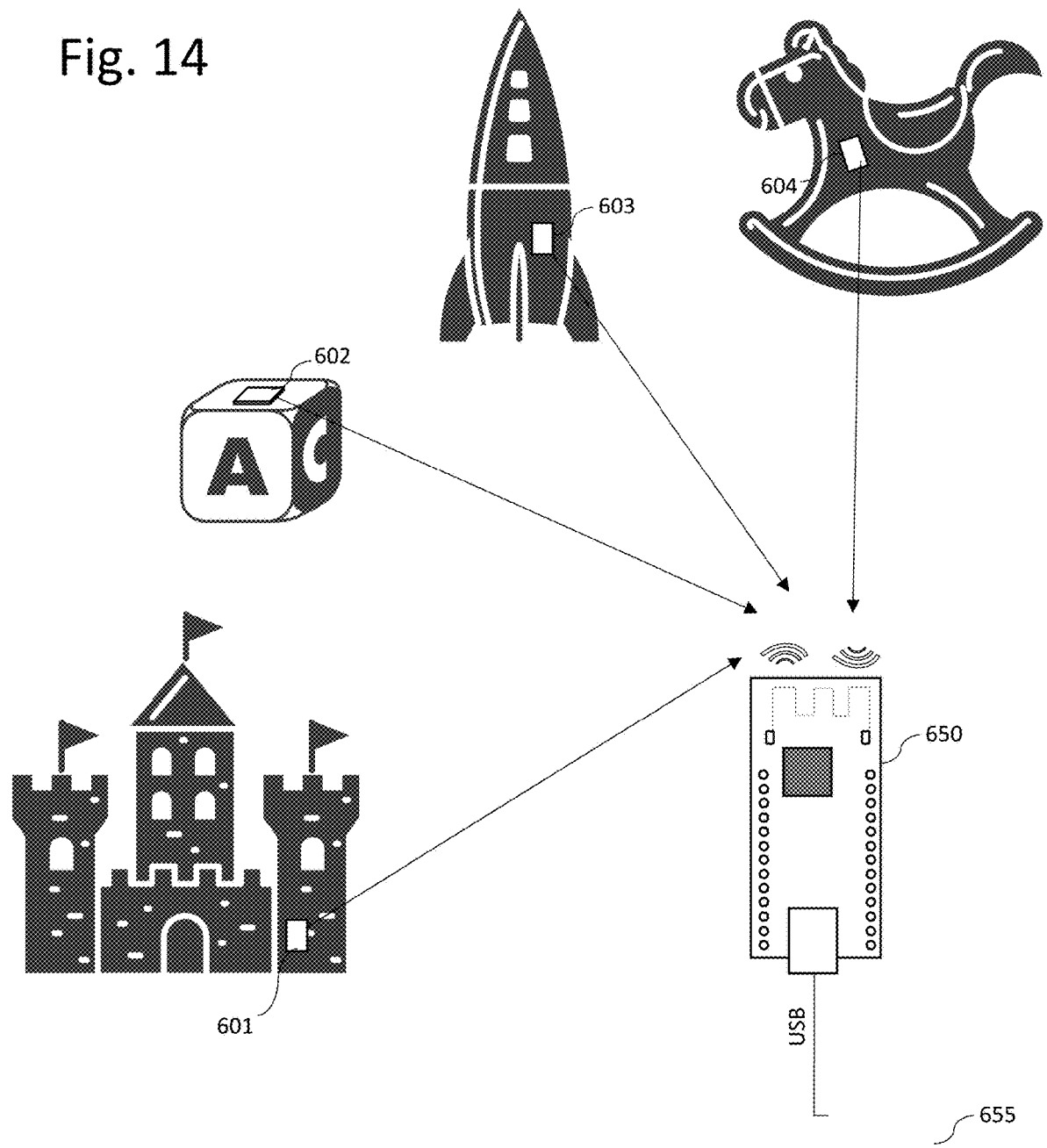
FIG. 14 is a diagrammatic view of a plurality of accelerometer-transceivers affixed to different toys for monitoring movement at a workstation computer.

FIG. 13 shows the compartmentalizing of battery 605, accelerometer 610 and first transceiver 615 into sensor housing 600. Sensor housing includes an activation LED 630, an activation switch 635 and an adhesive backing to affix the sensor onto an object. QR-code 625 allows registration of the sensor and to record its association with a particular toy in software running on computer workstation 655. Alternatively, simple linear bar codes and/or radio frequency identification chips (RFID) may be used as well. In FIG. 14, sensor 601 is affixed to a toy castle, sensor 602 is affixed to a letter block, sensor 603 is affixed to a toy rocket and sensor 604 is affixed to a rocking horse. It should be noted that these specific toys are exemplary only and other toys, common to therapy sessions, may be adopted and included within the technology of this invention. Sensors 601, 602, 603 and 604 may be initialized in low-power mode until such time accelerometer data brings them online and they transmit to second transceiver 655. This allows the system to automatically track which toys are engaged by the child throughout the play session giving the therapist greater freedom to interact and observe the child rather than to take manual notes on which toy and when it was played with.

Toys can be categorized into groups such as those to express feeling, exhibit aggression, cope with fear and the like. Each sensor QR-code is a unique identifier that associates the sensor not just with a specific toy, but also with a potential category of toy as well as a virtual avatar for the toy. The avatar, at its most basic form, is an image, typically a file format with transparency capability. It is a visual representation of the physical object. As an image, it can be segmented into heatmap localities, change colors, change size, and even animated as desired to convey associated manipulation of the physical counterpart by the child.

Avatars may be more advanced if desired, such as rigged, three-dimensional models of a physical object that mimic the articulation, movement and orientation of the physical object on the display interface.

At a basic level, accelerometer data conveys that the child is engaged in play with the object upon which the accelerometer is affixed. Therefore, as this data is transmitted, an automatic record of which toy is used for how long and in what manner is automatically logged by the computer processor and storage.

Figure 15:
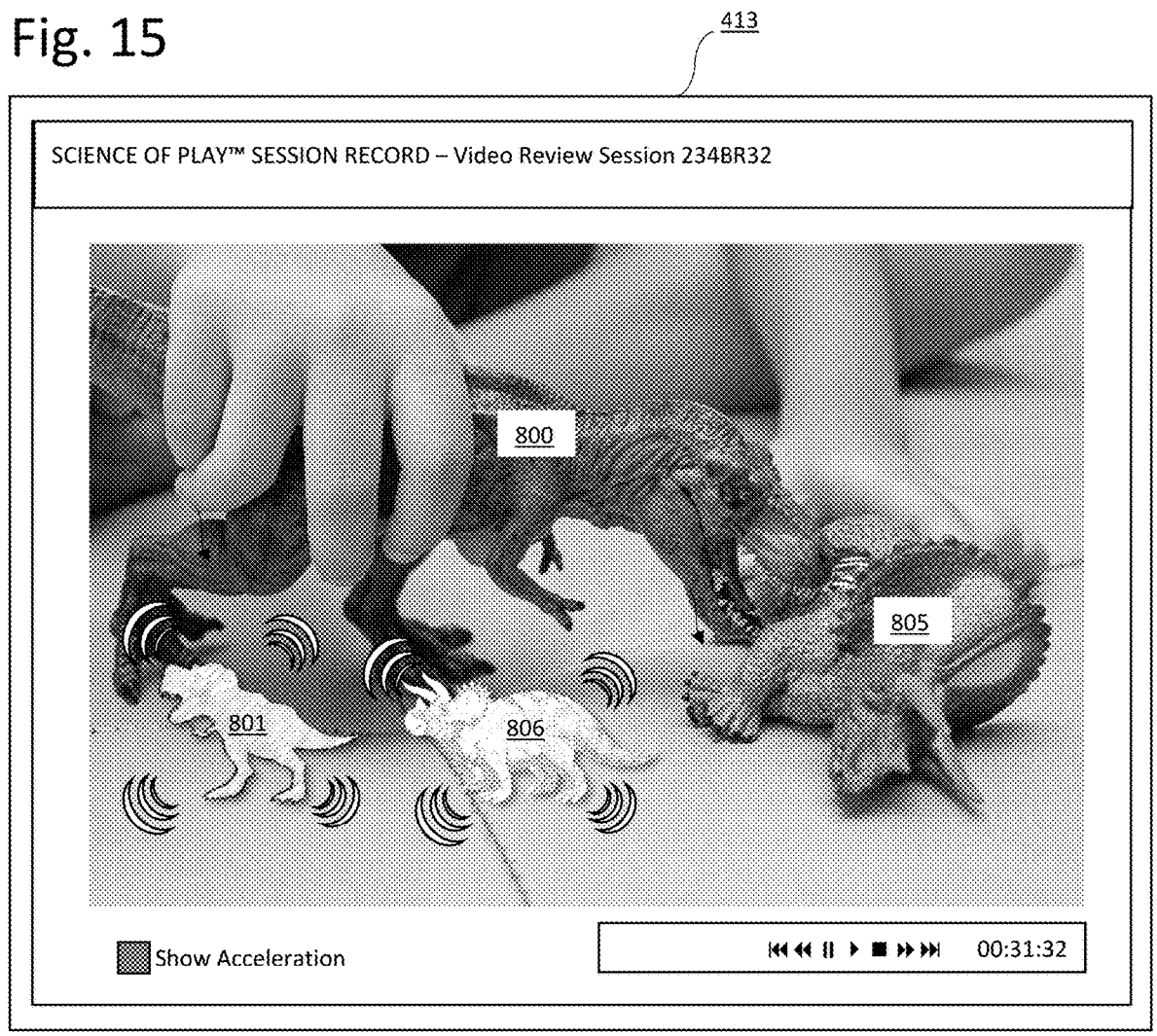
FIG. 15 is a graphic user interface showing a child playing with two dinosaur toys with an overlaid image of two corresponding avatars of each. The avatar renderings include indicia of movement from accelerometer data from the two physical toys.

As shown in FIG. 15, a plurality of toys (800 and 805) and associated avatars (801 and 806 respectively) may be analyzed together. Toys 800 and 805 were registered in a software application as dinosaur models. Accelerometer data received from sensors affixed to toys 800 and 805 register simultaneous movement of the two toys indicating the child may be engaging the toys with each other, particularly if the sensor data conveys high gravitational values. Logic in the software application might note interaction and engagement between two model dinosaurs is common across a history of play interaction sessions. However, because the accelerometer data not only conveys the time and gravitational values, but also the type of toy by virtue of its registration within the analytical software, abnormal interactions may be automatically identified. For example, if accelerometer data is received showing high gravitational values between two toys otherwise considered "incompatible" such as a dinosaur toy and an infant baby toy.

Figure 16:
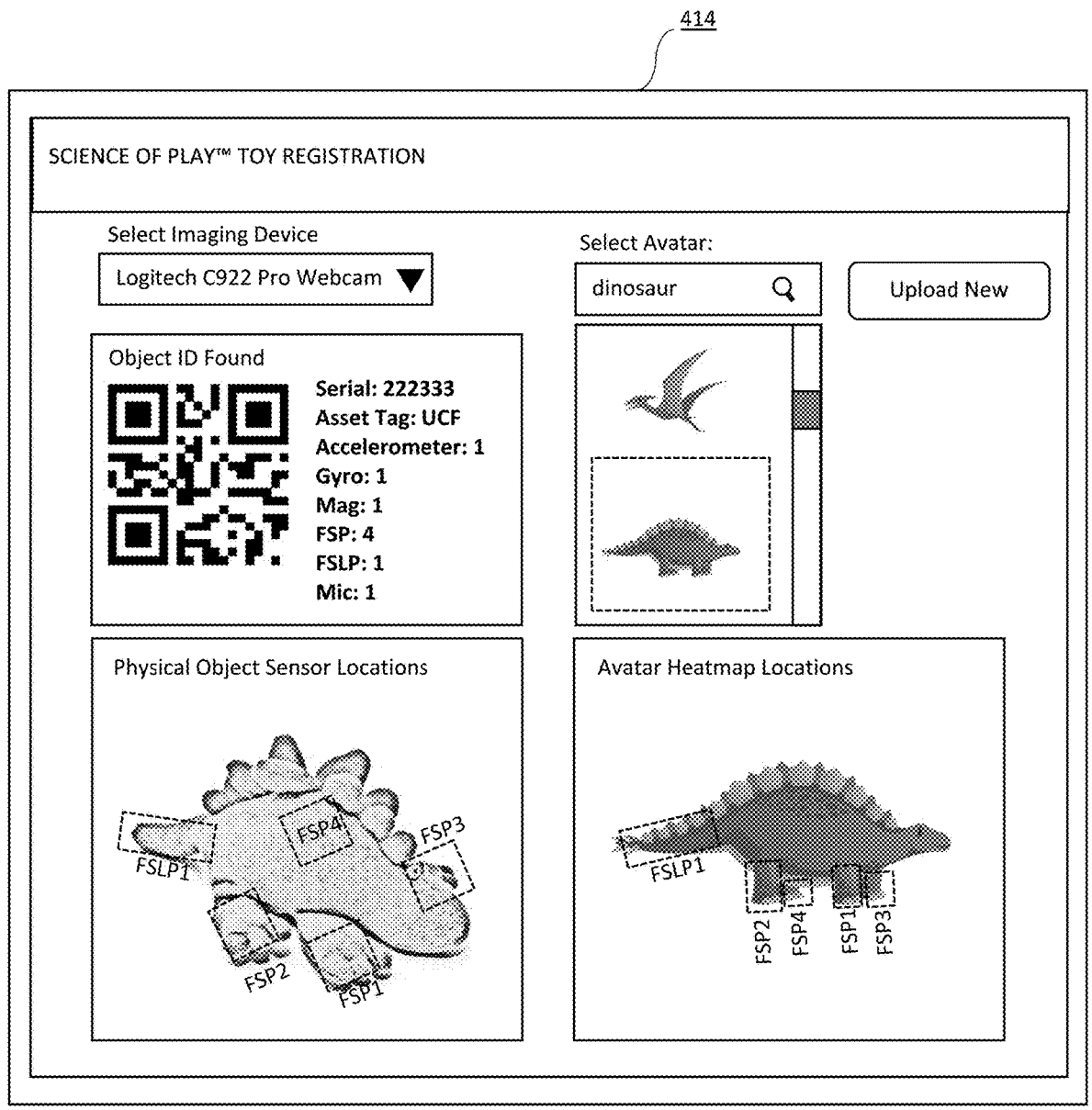
FIG. 16 is a graphic user interface showing the registration of a physical toy having a plurality of sensors and linking it to a computer-rendered avatar with heatmap localities associated with the pressure sensors on the physical toy.

Turning to FIG. 16, user interface 414 in the software application operable on a workstation intakes toys and sensors and registers them with the system. In the example of FIG. 16, a dinosaur toy branded SCIENCE OF PLAY™ Model 222333 is already known to have a predefined sensor array consisting of one accelerometer, one magnetometer, one 3-axis gyro, four FSPs about each leg, on FSLP (on the tail) and a microphone. An avatar for the physical object is selected and the locality heatmaps are positioned at the associated parts of the avatar to correlate with the physical toy. Thus, when a resistance drop is detected in at FSP1 on the physical toy, the avatar image is modified at the bounding box for FSP1 to convey the pressure imparted visually.

In an embodiment of the invention, a statistically viable population of known behavioral conditions are recorded, normalized and a pattern of sensor values and trends are associated with specific conditions to created "knowns." Subsequent clinical engagement with the same toys by "unknowns" are then analyzed using sensor value algorithm to determine if the current subject exhibits behavioral patterns associated with a known. Diagnostic results of the sensor data analysis are then displayed to a clinician.

Development Process

The initial development of this system is to be integrated into play therapy, a developmentally responsive approach to child counseling/therapy; however, the product is designed to be implemented in a variety of settings or uses (e.g., clinics, classrooms, at-home playrooms, universities, toy stores). Play therapy is a developmentally, responsive counseling approach for children and adults. Play therapists (i.e., child counselors) believe that play is a child's primary language and toys are their words or means to communicate effectively with others and their surroundings. Therefore, every toy in a traditional/standard playroom is selected with intentionality.

By documenting a child's interaction with toys, play therapists and other mental health professionals will be able to develop individualized treatment plans that are geared towards best practices, specific diagnoses/presenting issues, developmental age, ethnical, and gender considerations based on data-driven information collected through the Science of Play™ system. Big data gathered through this product/system will provide information on certain presenting diagnoses (i.e., Autism, ADHD, anxiety, ODD), necessary length of play sessions per diagnosis, appropriate treatment models per diagnosis to aid in the development of an individualized treatment plan as well as expand the scientific research base associated with developmental patterns discernable through play behaviors. In addition, data collected through this system provides specific markers based on neurotypical play behaviors as well as atypical play behaviors that may warrant additional follow-ups with medical providers, educators, psychiatrists, etc. Many behaviors are causes of medical diagnoses and not therapeutic treatment. The reverse is also true. Therefore, the Science of Play™ system will enable data-driven decisions to inform practitioners across fields of when to elicit integrative care from other professionals to best treat the child's symptomology.

The Science of Play™ is an innovative product that will extend established research of learning through play by developing new methodological tools that will apply state-of-the-art technologies to playrooms and play spaces. Specifically, the Science of Play™ will (a) deploy wireless, electronic tracking mechanisms on each toy/material found in a playroom to record the use (i.e., duration, frequency, and repetition) of the items; and (b) these tracking mechanisms will be synchronized to audio and video capture tools in order to (c) create a digital transcript of each therapeutic play session that (d) can be analyzed with machine learning algorithms to recognize developmental and abnormal patterns in play behavior.

Manualization of Data Coding and Integration

The current process to synthesizing data is taxing, labor intensive, and lacking in sophistication needed to comprehend the complexity of the data gathered. The current model consists of multiple teams of coders trained in various fields: play therapy, child development, computer visualization, kinesiology (for physiological data), machine learning, etc. Each field consists of its own team of coders. Coders are trained on the specific software and must reach inter-observer/coder reliability in order to code the data sets collected. Then the codes are inputted into a software system to visualize the overlap of data (see FIG. 1). However, a team of experts (e.g., Computer visualization analyst, play therapist, kinesiologist) across disciplines are needed for interpretation of the collected/coded data. The team discusses possible indicators for play behaviors and the synthesizing of the data for useable outcomes. In this model, there are several concerns: 1) loss of data at each step of the process, 2) manual labor needed for each recorded session of data (i.e., each session is 45 minutes), and 3) quantity of data needed to generate algorithms necessary for interpretable data outcomes (i.e., tens of thousands of data points). Therefore, there is a great need for the automation of this data for potential use across disciplines and professionals.

Automation Through Science of Play™ System.

Main products include: (1) Advances in research methodology: (1a) an electronic database that is capable of storing large data sets designed to integrate: (1b) wireless tracking mechanisms attached to each toy that transmits data (1c) audio and video capture with tracking data and (1d) physiological data (i.e., heart rate variability, accelerometer, skin conductance, and temperature); (2) Advances in theoretically-based conceptualization of play: (2a) automated coding of play behaviors, relational interactions, and physiological and psychological stress data, (2b) machine learning enabled pattern recognition (i.e., potential diagnoses, creativity, previously undetected child abuse, developmental milestones), (2c) recommendation system that offers suggestions for interventions and individualized treatment plans through personalized portal that links to an integrated care system in which referrals to other treatment providers can be generated.

(1a) Integrated system for collecting big data sets. This data will be auto-coded and integrated into data collected in 1a, 1b, and 1c. Due to the large amount of data collected, this data is saved into a repository designed specifically to manage big data sets.

(1b) Wireless tracking mechanism (e.g., transceiver combined with an accelerometer) that will be embedded and/or attached to each toy. This mechanism transmits automated data regarding the use (i.e., frequency, duration, and repetition) that a child plays and/or manipulates a toy/product. Due to the design of some of the standard toys in the playroom, we utilize a 3-D printer to print selected toys across the four agreed-upon categories of play to embed the mechanism in a less intrusive manner. For other toys in which tags are not easily embedded, we modify these tags in order to be connected in the least intrusive manner. The tag may use various materials to best fit the toys or items needed for tracking (i.e., sticker or cloth). In addition, the toys and manipulation of said toys will be auto-coded into the system for recognition: basic codes for toy categories (e.g., aggressive, creative, realistic, nurture) and advanced codes for play behaviors and play themes.

(1c) A system is provided that integrates audio (speech recognition) and video capture (cameras will be strategically placed in the playroom to visualize all aspects of child's face and play) with movement tracking data collected from the wireless tracking mechanism. Visually, an observer will be able to review the data regarding toy use and the child's verbal and non-verbal responses simultaneously for a more accurate assessment of the child's play.

(1d) Synthesizing of data includes physiological data of the child participant. Data is gathered via a wrist-based sensor for event-specific and session-level data to determine the efficacy of evaluation of physical activity tracking (accelerometry) and physiological stress monitoring (heart rate, electrodermal activity, and skin temperature) information. Specifically, the autonomic response to play therapy is evaluated through analysis of electrodermal activity via LEDALAB (or analogous software) to determine the sympathetic nervous system influence. Similar analysis is conducted examining the interbeat interval information via KUBIOS HRV (or analogous software) to determine the parasympathetic nervous system influence.

The tri-axial accelerometry data is compared with the video-based time-motion analysis from OBSERVER XT, while changes in skin temperature are considered as a potential stress response indicator. The inclusion of this information provides valuable insight regarding behavioral changes over time and understanding reactions and stress responses to external stimuli (i.e., therapists' responses, teacher instruction, medical procedures) for more targeted interactions that mitigate stress while simultaneously improving the child's overall outcomes, specifically in the play therapy process for the initial development.

(2a & 2b) This product utilizes applications of artificial intelligence and machine learning. Based on codes integrated within the product from experts in fields of play therapy, kinesiology, child development, over time and with more data (i.e., machine learning), the product recognizes patterns of play behaviors and discern themes within a single session and across multiple sessions. The algorithms process data collected across platforms such as audio, visual, physical activity tracking (accelerometry), and physiological stress monitoring (heart rate, electrodermal activity, and skin temperature) information, eliminating the need for multiple platforms (i.e., OBSERVER XT, LEDALAB, KUBIOS HRV), and manual coding and integration of the raw material. The automation of synthesizing this data mitigates the personnel shortage across disciplines, in particular the field of mental health (e.g., play therapy).

(2c) A recommendation system offers suggestions for interventions and individualized treatment plans based on child's developmental level (neurotypical, atypical play behaviors), age, ethnicity, gender, presenting concerns, etc. Automated reports are generated to summarize play within a single session or across a specific period of time from multiple sessions. The recommendation system is linked to an integrative care portal in which referrals can automatically be sent to relevant providers across disciplines to provide best care practices for the child. Also, within the dashboard are options for international work. For example, the information will be computed based on language selected (i.e., English, German, French, Spanish, Mandarin, etc.) and the coding function is inclusive of specific toys pertinent to the culture selected.

Intellectual Merit:

Current policy debates about the merits of play are often conducted in the absence of sound theory and empirical evidence. The disclosed technology to develop the Science of Play™ will initiate the development of big data projects in the field of play and facilitate high quality research.

Broader Impacts:

This technology is useful for a variety of disciplines for enhancing current training, practice, or research initiatives. Therefore, project activities directly impact students, teachers, school districts, and subsequently informs the professions of counseling and education by fostering evidence-based practice concerning the understanding of free play on learning, cognitive development, and problem-solving skills. Currently, there is no database on play and play behaviors. This project will demonstrate the feasibility of creating a large-scale database that can be analyzed across disciplines, enhancing the scalability to beyond free play within educational settings.

With the shift towards integrative care in medical field, to include mental health, this system enables quick synthesis and recommendations based on the integrated data collected. Recommendations are shared via a portal system across professional fields, including but not limited to mental health, education, medicine. Professionals in the field or university professors may use the data integrated system to enhance education and learning of current students or new professionals by informing best practices to embed within the classroom or advanced training, to aid in training of accurate, individualized, treatment plans, and to test students' gained knowledge within the classroom based on accuracy of report. In addition, researchers, in both private and public industries, may utilize this system to collect data on children's behavioral responses to various toys—new, old, or toys based on developmental need by embedding wireless trackers to develop data regarding use, duration, and frequency of toys in piloting testing to better market their products.

For example, children may have visceral responses to certain toys that could elicit fear or excitement. This system provides accurate, quick synthesized data to determine appropriate toys based on child's development level or recent experience (i.e., natural disaster, school shooting, divorce, abuse, new baby, etc.). This information is then marketed to parents to help in appropriate toy selection based on developmental age or experiences.

In addition, this system can assist in the development of mobile labs that can connect to any device (i.e., IPAD, IPHONE) to connect data on child's over well-being. For example, a mobile lab could be set up in an elementary school during kindergarten registration, after a natural disaster, or school shooting to aid in understanding the child's developmental milestones and behavioral/stress responses in order to provide most supportive care when child attends school or post-events. Similarly, a mobile lab could be set up on a designated day of the month at a pediatricians' office for any child who may not be aligning with paper and pencil milestone checklists for further assessment.

Computer and Software Technology

The present invention may be embodied on various platforms. The following provides an antecedent basis for the information technology that may be utilized to enable the invention.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

The machine-readable medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device. Storage and services may be on premise or remote such as in the "cloud" through vendors operating under the brands, MICROSOFT AZURE, AMAZON WEB SERVICES, RACKSPACE, and KAMATERA.

A machine-readable signal medium may include a propagated data signal with machine-readable program code embodied therein, for example, in baseband or as part of a carrier wave. Such a propagated signal may take any of a variety of forms, including, but not limited to, electro-magnetic, optical, or any suitable combination thereof. A machine-readable signal medium may be any machine-readable medium that is not a computer readable storage medium and that can communicate, propagate, or transport a program for use by or in connection with an instruction execution system, apparatus, or device. However, as indicated above, due to circuit statutory subject matter restrictions, claims to this invention as a software product are those embodied in a non-transitory software medium such as a computer hard drive, flash-RAM, optical disk or the like.

Program code embodied on a machine-readable medium may be transmitted using any appropriate medium, including but not limited to wireless, wire-line, optical fiber cable, radio frequency, etc., or any suitable combination of the foregoing. Machine-readable program code for carrying out operations for aspects of the present invention may be written in any combination of one or more programming languages, including an object-oriented programming language such as Java, C #, C++, R, Visual Basic or the like and conventional procedural programming languages, such as the "C" programming language or similar programming languages. Additional languages may include scripting languages such as PYTHON, LUA and PERL.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by machine-readable program instructions.

Glossary and Components

Accelerometer means an electronic device that measure accelerations, which is the rate of change of the velocity of an object. Acclerometers measure in meters per second squared ($m/s^2$) or in G-forces (g). A single G-force on planet Earth is equivalent to 9.8 $m/s^2$, but this does vary slightly with elevation. Accelerometers are useful for sensing vibrations in systems or for orientation applications. Accelerometers can measure acceleration on one, two, or three axes. Generally, accelerometers contain capacitive plates housed internally. Some plates are fixed, while others are attached to small springs that move internally as acceleration forces act upon the sensor. As these plates move in relation to each other, the capacitance between them changes. From these variances in capacitance, the acceleration can be resolved.

Battery is a device consisting of one or more electrochemical cells with external connections for powering electrical devices such as microcontrollers, active sensors and passing current through passive sensors for detecting changes in resistance.

Computer workstation is a computing device loosely to refer to everything from a mainframe computer terminal to a personal computer connected to a network. For the purposes of this application, "workstation" is used to refer to the external computing system receiving sensor data from an embedded microcontroller inside a physical toy (the microcontroller technically also a computing system). The computer workstation term is used herein broadly as video capture of a play therapy session may be stored directly to a network attached storage device accessible through a local area network (or wide area network) by the workstation. Furthermore, rendering of an integrated video record of a play session with a computer-generated avatar conveying sensor data may be sent to a rendering farm (e.g., a cloud-hosted processor) that has more powerful graphic processing units then returns (or makes downloadable or streamable) the diagnostic video record to the workstation or other device capable of displaying the information.

Controls means user interface buttons, links and other display input components on a graphic user interface to facilitate selection of a heatmap locality, timecode value or sensor field. In one example enumerated above, the heatmap locality on the avatar is "clickable" to cause the software to cue up the video record of the play session to the point in time in which the heatmap locality reached a maximum or minimum value.

Digital camera means a camera that captures moving images (and usually audio as well) and encodes it as digital data.

Input/Output (I/O) means a connection between an information processing system, such as a computer, and the outside world (such as sensors).

Locality heatmap is a data visualization method that shows magnitude of a value as color in two dimensions. The variation in color may be by hue, shading or intensity, giving clear visual cues to the observer about how a quantitative phenomenon is clustered or varies over space.

Microcontroller means a small computer on a single metal-oxide-semiconductor (MOS) integrated circuit chip. A microcontroller contains one or more CPUs (processor cores) along with memory and programmable input/output peripherals.

Polling means actively sampling the status of an external device by a client program as a synchronous activity. Polling is most often used in terms of input/output (I/O).

Pressure sensor in this application refers to passive components such as force-sensing resistors that exhibit a decrease in resistance when there is an increase in the force applied to the active area.

Processor means an electronic circuit which performs operations on some external data source, usually memory or some other data stream.

Resistance means a measure of its opposition to the flow of electric current.

The inverse quantity is electrical conductance which is the ease with which an electric current passes.

Speech to Text means the recognition and translation of spoken language into text by computers from an audio stream.

Storage device means a repository to archive and report digital information.

Synchronization means the coordination of the sensor values with the audiovisual record of the play session so that the information may be conveyed in unison. This may be done by synchronizing the compute workstation time and microcontroller time with a reference value so the timecode on each device (sensor and video) may be aligned. Another option is to record an audio stream from the physical toy and align the audio of the toy (timecoded with the sensor data) to the audio of the web cam videoing the play session.

Therapy session means the time during which the child, and possibly accompanied by a therapist or clinician, is videoed interacting with toys.

Timecode is a sequence of numeric codes generated at regular intervals by a timing synchronization system. Timecode is used in video production, show control and other applications which require temporal coordination or logging of recording or actions.

Toy (avatar) is a virtual representation of a physical toy used in play during a play session. The avatar of the toy permits a synchronized graphic representation of forces, movement, pressure and other quantitative impacts on the physical counterpart. Furthermore, the avatar may convey computationally derived expressions from logical processing of sensor data. For example, "happy" or "fearful" expressions on an avatar based on the values of the sensor data.

Toy (physical) is a physical item that is used in play, especially one designed for such use. In the context of this application, the toy has at least one sensor or indicium permitting the interaction with the physical item to be monitored and quantified.

Transceiver means a device able to receive information over a wireless medium and also send out information over the medium. The most common example of this is RF (Radio Frequency) technology.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. An apparatus for play therapy diagnostics and treatment, the apparatus comprising:
   a microcontroller affixed inside a physical toy, the microcontroller having an embedded operating system reading stored instructions to execute functions and procedures according to computer-readable code;
   a battery secured inside the physical toy and electrically coupled to the microcontroller to power it;
   a plurality of pressure sensors affixed inside or upon the surface of the physical toy, the sensors communicatively coupled to the microcontroller through an input/output (I/O) connection, the pressure sensors configured to detect force imparted upon the sensor measured by a resistance drop to electrical current running through each sensor, each sensor connected through a dedicated I/O connection wherein the microcontroller contains instructions to poll the plurality of pressure sensors for a value representative of electrical resistance;
   an accelerometer affixed inside or upon the surface of the physical toy, the accelerometer communicatively coupled to the microcontroller through another dedicated I/O connection whereby gravitational forces imparted on the physical toy are sensed by the accelerometer and communicated to the microcontroller;

a transceiver affixed inside or upon the surface of the physical toy, the transceiver communicatively coupled to the microcontroller and configured to transmit data collected by the pressure sensors and accelerometer to an external transceiver;

a computer workstation having a processor and computer-readable memory storing software for executing functions and procedures on the processor;

a digital camera configured to capture video of a play therapy session including at least one child interacting with the physical toy, the digital camera configured to encode an audiovisual stream into a storage device as stored video accessible by the processor;

a connection from the processor to the external transceiver, the external transceiver receiving timecoded accelerometer and pressure sensor data from the microcontroller in the physical toy during the play therapy session;

computer readable instructions in the computer workstation memory for generating an avatar of the physical toy and visually modifying the avatar responsive to pressure sensor data received from the microcontroller; and a display device communicatively coupled to the computer workstation, configured to display the avatar and stored video of the play therapy session, wherein the modification of the visual representation of the avatar responsive to pressure sensor data is synchronized with the stored video.

2. The apparatus of claim 1 further comprising software to cause the microcontroller to:

retrieve resistance values for each pressure sensor by polling each pressure sensor at least once per second;

execute a function to retrieve a timecode value from a clock embedded in the microcontroller; and transmit through the first transceiver to the external receiver, the resistance values for each pressure sensor associated with the timecode value when the resistance value was obtained.

3. The apparatus of claim 2 further comprising software to cause the processor on the computer workstation to:

store each pressure sensor reading associated with the time code value when the resistance value was obtained;

parse all the resistance values for each pressure sensor to retrieve the minimum resistance value for each sensor with the associate timecode representative of the time during the therapy session when the value occurred; and for each pressure sensor, enumerate on the display device, the location on the physical toy where the pressure sensor is located, the minimum value of resistance detected and the timecode value of when the minimum value occurred during the therapy session.

4. The apparatus of claim 3 wherein the enumerated pressure sensor location, minimum value of resistance and timecode value are independently selectable as controls by end user input whereby upon selection of a control, the stored video is played on the display device at the timecode value of the selected control.

5. The apparatus of claim 4 whereby a speech-to-text generated transcript of the therapy session is presented in timed synchronization with the stored video.

6. The apparatus of claim 4 wherein the avatar of the toy is shown on the display device concurrently with the stored video, the avatar of the toy having a locality heatmap of each pressure sensor generated in synchronization with the resistance measured at each timecode value.

7. The apparatus of claim 3 further comprising an array of pressure sensor resistance range values stored in memory accessible by the processor, each range value is associated with a distinct level of visual modification to the portion of the avatar of the toy representative of the corresponding portion of the physical toy where the pressure sensor is affixed.

8. The apparatus of claim 7 wherein the distinct level of visual modification is a change in color of the portion of the avatar of the toy.

9. The apparatus of claim 1 wherein the gravitational forces detected by the accelerometer in the physical toy cause the software operable on the computer workstation to convey through the display device that the child is manipulating that specific toy during the therapy session and displaying an associated avatar of the physical toy concurrently with the stored video on the display device.

* * * * *